United States Patent [19]

Heeres et al.

[11] 4,368,200

[45] Jan. 11, 1983

[54] HETEROCYCLIC DERIVATIVES OF (4-PHENYL-PIPERAZINE-1-YL-ARYLOX-YMETHYL-1,3-DIOXOLAN-2-YL)-METHYL-1H-IMIDAZOLES AND 1H-1,2,4-TRIAZOLES

[75] Inventors: Jan Heeres, Vosselaar; Leo J. J. Backx, Arendonk, both of Belgium

[73] Assignee: Janssen Pharmaceutica N.V., Beerse, Belgium

[21] Appl. No.: 224,992

[22] Filed: Jan. 14, 1981

Related U.S. Application Data

[60] Division of Ser. No. 20,383, Mar. 14, 1979, Pat. No. 4,267,179, which is a continuation-in-part of Ser. No. 919,333, Jun. 23, 1978, abandoned.

[51] Int. Cl.³ .................. A61K 31/495; C07D 405/14
[52] U.S. Cl. .................................... 424/250; 544/366; 544/370; 544/371; 544/372; 548/262; 548/341
[58] Field of Search ...................... 544/366, 370, 371; 424/250

[56] References Cited

U.S. PATENT DOCUMENTS

| | | | |
|---|---|---|---|
| 3,898,230 | 8/1975 | Regnier et al. | 544/366 |
| 3,936,470 | 2/1976 | Heeres | 424/273 |
| 4,144,346 | 3/1979 | Heeres et al. | 424/273 |

*Primary Examiner*—Donald G. Daus
*Assistant Examiner*—James H. Turnipseed
*Attorney, Agent, or Firm*—Geoffrey G. Dellenbaugh

[57] ABSTRACT

Novel heterocyclic derivatives of (4-phenylpiperazin-1-yl-aryloxymethyl-1,3-dioxolan-2-yl)methyl-1H-imidazoles and 1H-1,2,4-triazoles, useful as antifungal and antibacterial agents.

7 Claims, No Drawings

HETEROCYCLIC DERIVATIVES OF (4-PHENYL-PIPERAZINE-1-YL-ARYLOXYMETH-YL-1,3-DIOXOLAN-2-YL)-METHYL-1H-IMIDAZOLES AND 1H-1,2,4-TRIAZOLES

CROSS-REFERENCE TO RELATED APPLICATIONS:

This is a division of application Ser. No. 20,383, filed Mar. 14, 1979, now U.S. Pat. No. 4,267,179, which in turn is a continuation-in-part application of Ser. No. 919,333, filed June 23, 1978, now abandoned.

BACKGROUND OF THE INVENTION:

In U.S. Pat. No. 3,936,470 and Belg. Pat. No. 837,831 there are described a number of 1-(1,3-dioxolan-2-ylmethyl)-1H-imidazoles and 1H-1,2,4-triazoles having antifungal and antibacterial properties. The compounds of this invention differ from the foregoing essentially by the substitution of the aryloxy-moiety with a 4-phenyl-piperazinyl group, wherein said phenyl is further substituted with a heterocyclic radical which is attached to the phenyl group by a carbon-nitrogen bond. Similar compounds wherein a heterocyclic radical is attached directly to the aryloxy group by a carbon-nitrogen bond are described in U.S. Pat. appln. Ser. No. 853,726, filed Nov. 21, 1977.

DESCRIPTION OF THE PREFERRED EMBODIMENTS:

This invention is concerned with novel 1H-imidazole and 1H-1,2,4-triazole derivatives which may structurally be represented by the formula:

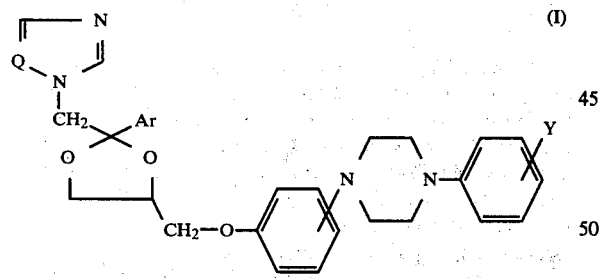

(I)

and the pharmaceutically acceptable acid addition salts and stereochemically isomeric forms thereof, wherein:

Q is a member selected from the group consisting of CH and N;

Ar is a member selected from the group consisting of phenyl, thienyl, halothienyl and substituted phenyl, said substituted phenyl having from 1 to 3 substituents each independently selected from the group consisting of halo, lower alkyl, lower alkyloxy and trifluoromethyl; and the radical Y is a member selected from the group consisting of a 1H-pyrrol-1-yl radical of the formula

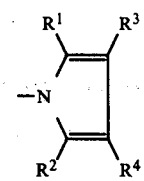

(a)

wherein $R^1$, $R^2$, $R^3$ and $R^4$ are each independently selected from the group consisting of hydrogen, lower alkyl, aryl and aryl-lower alkyl;

a 1H-pyrazol-1-yl radical of the formula

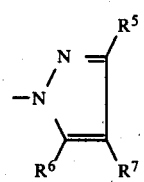

(b)

wherein $R^5$, $R^6$ and $R^7$ are each independently selected from the group consisting of hydrogen, lower alkyl, aryl and aryl-lower alkyl;

a 1H-imidazol-1-yl radical of the formula

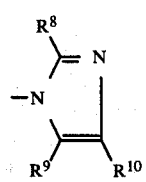

(c)

wherein $R^8$ is selected from the group consisting of hydrogen, lower alkyl, mercapto, lower alkylthio and aryl-lower alkylthio, and $R^9$ and $R^{10}$ are each independently selected from the group consisting of hydrogen, lower alkyl, aryl and aryl-lower alkyl;

a 1H-1,2,4-triazol-1-yl radical of the formula

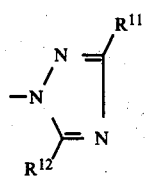

(d)

wherein either of $R^{11}$ and $R^{12}$ is selected from the group consisting of hydrogen, hydroxy, mercapto, lower alkylthio and aryl-lower alkylthio, the remaining being selected from the group consisting of hydrogen, lower alkyl and aryl-lower alkyl;

a 4H-1,2,4-triazol-4-yl radical of the formula

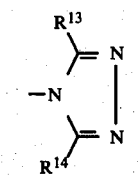

(e)

wherein $R^{13}$ is selected from the group consisting of hydrogen, mercapto, hydroxy, lower alkylthio and aryl lower alkylthio, and $R^{14}$ is selected from the group consisting of hydrogen lower alkyl, aryl and aryl-lower alkyl;

a 2,3-dihydro-4H-1,2,4-triazol-4-yl radical of the formula

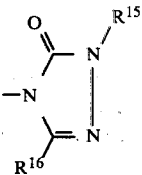

wherein $R^{15}$ is selected from the group consisting of lower alkyl and aryl-lower alkyl and $R^{16}$ is selected from the group consisting of hydrogen, lower alkyl, and aryl-lower alkyl;

a 1H-1,2,3,4-tetrazol-1-yl radical of the formula

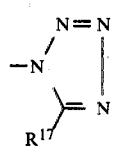

wherein $R^{17}$ is selected from the group consisting of hydrogen, mercapto, lower alkyl, aryl and aryl-lower alkyl;

wherein said aryl as used in the foregoing definitions is selected from the group consisting of phenyl and substituted phenyl, said substituted phenyl having from 1 to 3 substituents each independently selected from the group consisting of halo, lower alkyl, lower alkyloxy and trifluoromethyl.

It is understood that radicals of formulas (c) and (g) wherein $R^8$, respectively $R^{17}$, stand for mercapto, as well as radicals of formulas (d) and (e) wherein $R^{11}$ or $R^{12}$, respectively $R^{13}$, stand for mercapto or hydroxy, may also exist in their tautomeric thioxo, respectively oxo, forms. Such thioxo and oxo forms, although not explicitely indicated in the above structures, are naturally intended to be within the scope of formula (I).

The preferred compounds of this invention are those where the 4-phenylpiperazinyl function is attached to the phenoxymethyl moiety in the para position.

As used in the foregoing and in following definitions the term "halo" is generic to fluoro, chloro, bromo and iodo; and "lower alkyl" is meant to include straight and branched hydrocarbon radicals having from 1 to 6 carbon atoms such as, for example, methyl, ethyl, 1-methylethyl, 1,1-dimethylethyl, propyl, 1-methylpropyl, 2-methylpropyl, butyl, pentyl, hexyl and the like.

In order to simplify the structural representation of the compounds (I) and of certain starting materials and intermediates used in the preparation thereof, the 2-Ar-2-(1H-imidazol-1-ylmethyl or 1H-1,2,4-triazol-1-ylmethyl)-1,3-dioxolan-4-yl group, wherein Ar is as previously defined, will hereinafter be represented by the symbol D:

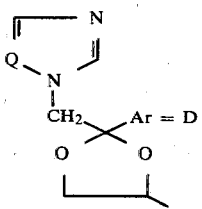

Q=CH or N

The compounds of formula (I) wherein Y is as previously defined, but other than a radical of formula (c) or (g) wherein $R^8$, respectively $R^{17}$, is mercapto and other than a radical of formula (d) or (e) wherein $R^{11}$ or $R^{12}$, respectively $R^{13}$, is mercapto or hydroxy, said Y being represented by Y' and said compounds being represented by the formula (I'), can be prepared by O-alkylating an appropriate phenol of formula (III) with a reactive ester of formula (II).

D—CH$_2$—W +

(II)

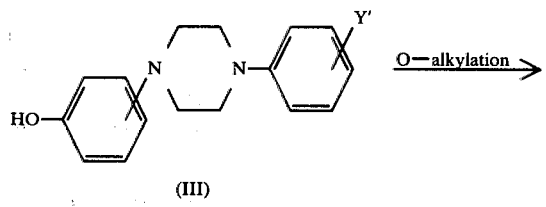

(III)

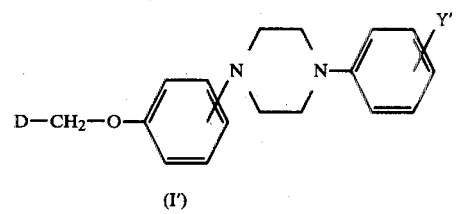

(I')

In formula (II), W has the meaning of a reactive ester residue such as, for example, halo, preferably chloro, bromo or iodo, or a sulfonyloxy group such as, for example, methylsulfonyloxy or 4-methylphenylsulfonyloxy and the like. The reaction of (II) with (III) is carried out under art-known conditions of performing O-alkylations with reactive esters. The reaction is generally carried out in an appropriate reaction-inert organic solvent such as, for example, N,N-dimethylformamide, N,N-dimethylacetamide, hexamethylphosphoric triamide, dimethylsulfoxide, 4-methyl-2-pentanone and the like, optionally in admixture with other reaction-inert solvents such as, for example, aromatic hydrocarbons, e.g., benzene, methylbenzene, dimethylbenzene and the like. Further it is advantageous to add to the reaction mixture an appropriate base such as, for example, an alkali metal hydride or carbonate, in order to enhance the rate of the reaction. Otherwise it may be advantageous to first convert the substituted phenol (III) into a metal salt thereof, preferably the sodium salt, in the usual manner, e.g., by the reaction of (III) with metal bases such as sodium hydride, sodium hydroxide and the like, and to use thereafter said metal salt in the reaction with (II). Somewhat elevated temperatures are appropriate to enhance the reaction rate and most preferably the reaction is carried out at from about 80° C. to about 130° C.

The compounds of formula (I), wherein Y is as previously defined, can generally be prepared by cyclizing an intermediate of formula (IV) with an appropriately substituted aminobenzene of formula (V).

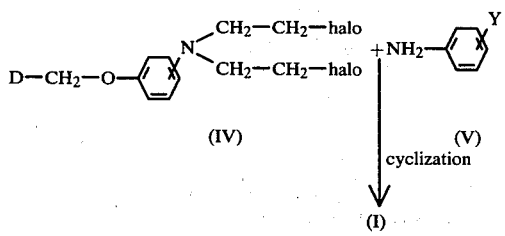

The reaction is carried out by stirring the reactants together in the presence of an appropriate polar solvent, e.g., water, in admixture with an appropriate water-miscible organic solvent such as, for example, 2-propanol, 2-propanone and the like, preferably at an elevated temperature, in order to enhance the rate of the reaction, and, most preferably, in the presence of an appropriate alkali- or earth alkali metal iodide such as, for example, potassium iodide.

The compounds of formula (I) can alternatively be prepared by N-alkylating a compound of formula (VI) with an appropriately substituted halo-benzene of formula (VII), following standard N-alkylating procedures.

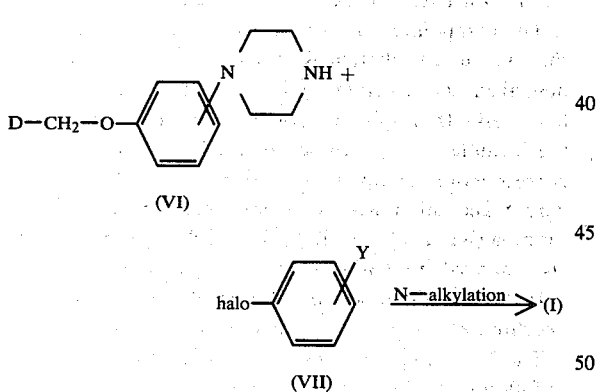

Said N-alkylation may be carried out in the usual manner, e.g., by stirring the reactants together, preferably at somewhat elevated temperatures in an appropriate organic solvent such as, for example, dimethylsulfoxide, dimethylformamide and the like, in the presence of an appropriate base such as, for example, an alkali metal hydride or carbonate.

Still another method of preparing the compounds of formula (I) is by cyclizing an appropriate intermediate of formula (VIII), wherein A is an amino group or a suitable derivative thereof, with an appropriate cyclizing agent, following art-known procedures, and, if desired, introducing substituents into the thus obtained heterocyclic compounds.

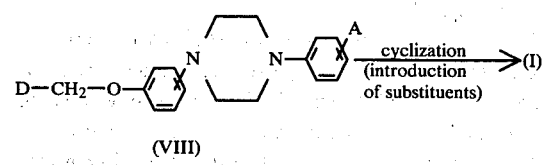

The nature of A in formula (VIII), as well as the nature of the cyclizing agent to be used in the cyclization step, depend upon the meaning of Y in the desired compounds (I) as will be explained hereafter in more detail.

The compounds of formula (I) wherein Y stands for the radical (a), wherein $R^1$, $R^2$, $R^3$ and $R^4$ have the previously defined meaning, said compounds being represented by the formula (I-a), can be derived from an appropriate amine of formula (VIII-a), by cyclizing the latter with an appropriate dione of formula (IX-a) or a tetrahydro-2,5-di(lower alkyloxy)furan of formula (IX-b).

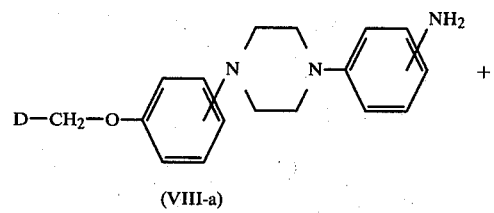

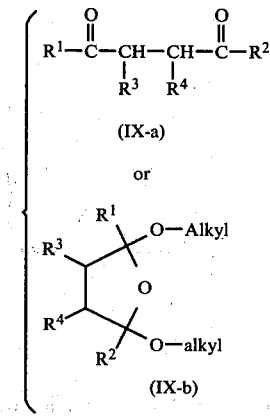

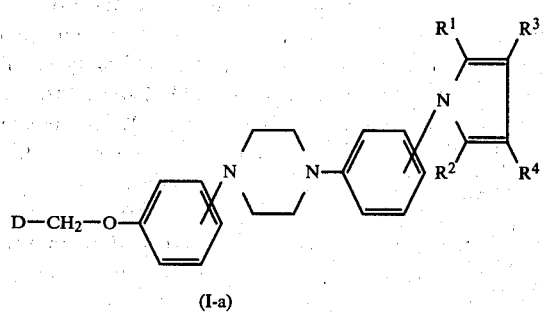

The reaction of (VIII-a) with (IX-a) is conveniently carried out by stirring and refluxing the reactants together in an appropriate solvent, e.g., a lower alkanol such as ethanol and the like, preferably, but not necessarily, in the presence of an appropriate base such as, for example, an alkali metal carbonate, e.g., potassium carbonate and the like. The reaction of (VIII-a) with (IX-b)

is preferably carried out in a polar solvent, e.g., acetic acid and the like.

The compounds of formula (VIII-a), used as intermediates herein, display strong antifungal and antibacterial properties themselves and both as useful intermediates herein and as antifungal and antibacterial substances they constitute an additional feature of this invention.

The compounds of formula (I) wherein Y stands for the radical (b), wherein $R^5$, $R^6$ and $R^7$ have the previously defined meaning, said compounds being represented by the formula (I-b), can be derived from an appropriate hydrazine of the formula (VIII-b), which is usually employed in the form of an acid addition salt, by cyclizing the latter with an appropriate dione of formula (X).

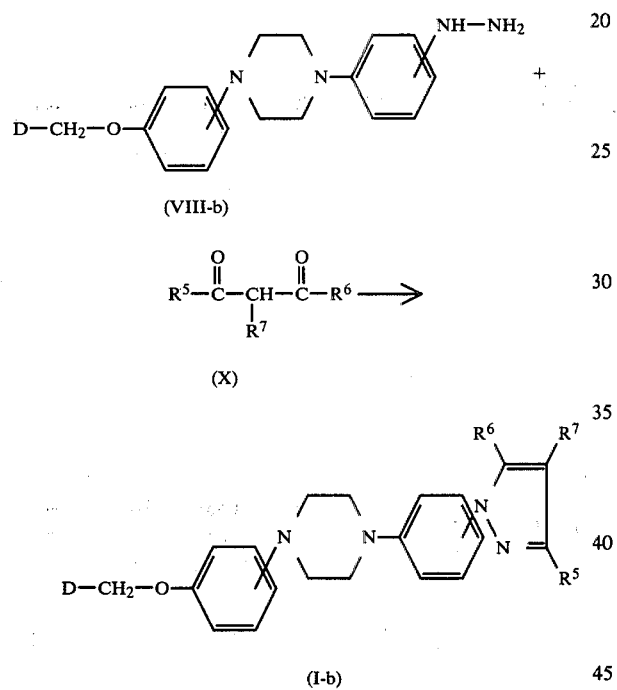

The reaction of (VIII-b) with (X) is carried out following the same procedure as for the preparation of (I-a) starting from (VIII-a) and (IX-a). When $R^5$ is hydrogen, the adjacent carbonyl group of (X) is preferably acetalized prior to reacting said (X) with (VIII-b) in order to obtain a pyrazole derivative wherein $R^6$ is unambiguously located at the 5-position. Mixtures of position isomers which can otherwise be obtained when using unacetalized aldehydes or ketones of formula (X) may be subjected to standard isolation and purification procedures to separate the pure constituents from each other.

The compounds of formula (I) wherein Y stands for a radical (c) wherein $R^9$ and $R^{10}$ are as previously defined and wherein $R^8$ stands for mercapto, said compounds being represented by the formula (I-c-1), can be prepared by cyclizing an appropriate isothiocyanate of formula (VIII-c) with an appropriate amino-ethanone or amino-acetaldehyde of formula (XI).

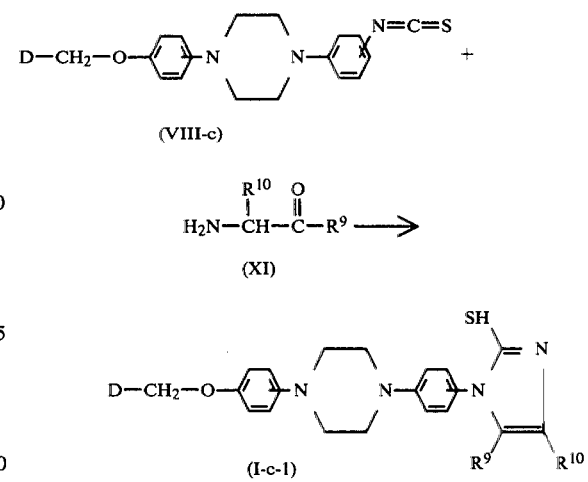

The reaction of (VIII-c) with (XI) is conveniently carried out by stirring, preferably under heating, the reactants together in a suitable organic solvent, such as a lower alcohol, e.g., 2-propanol, in the presence of an appropriate base such as, for example, an alkali or earth alkali metal carbonate or hydrogen carbonate.

The compounds of formula (I) wherein Y stands for the radical (c) wherein $R^9$ and $R^{10}$ are as previously defined and wherein $R^8$ stands for hydrogen, said compounds being represented by the formula (I-c-2), can easily be obtained by desulfurating a compound of formula (I-c-1) in the usual manner, e.g., by treating the latter with Raney nickel or with diluted nitric acid.

The compounds of formula (I) wherein Y represents the radical (c) wherein $R^9$ and $R^{10}$ are as previously described and wherein $R^8$ is lower alkylthio or aryl-lower alkylthio, said compounds being represented by the formula (I-c-3), can be prepared by subjecting the corresponding compounds of formula (I-c-1) to a standard S-alkylation with a suitable reactive ester of the formula (XII), wherein $R^8_a$ is lower alkyl or aryl-lower alkyl and wherein W is as previously defined.

In turn the compounds of formula (I-c-3) may be desulfurated yielding the compounds of formula (I-c-2).

The foregoing reactions are schematically illustrated as follows:

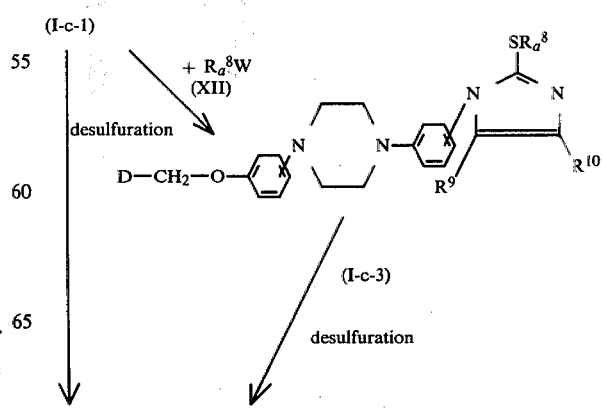

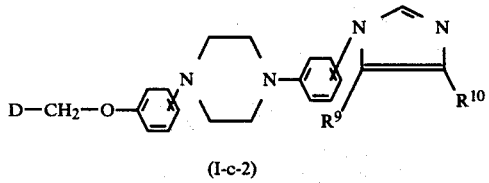

(I-c-2)

solvent, e.g., a lower alkanol such as, for example, 2-propanol, butanol and the like.

The compounds of formula (I-d-1) may alternatively be prepared by first acylating (VIII-d-1) with an appropriate anhydride (XIII-b) or an alkanoyl halide (XIII-c), derived from a carboxylic acid (XIII), to obtain an intermediate of formula (XIV), and, subsequently, cyclizing the latter by stirring and heating (XIV) in an alcoholic alkaline medium.

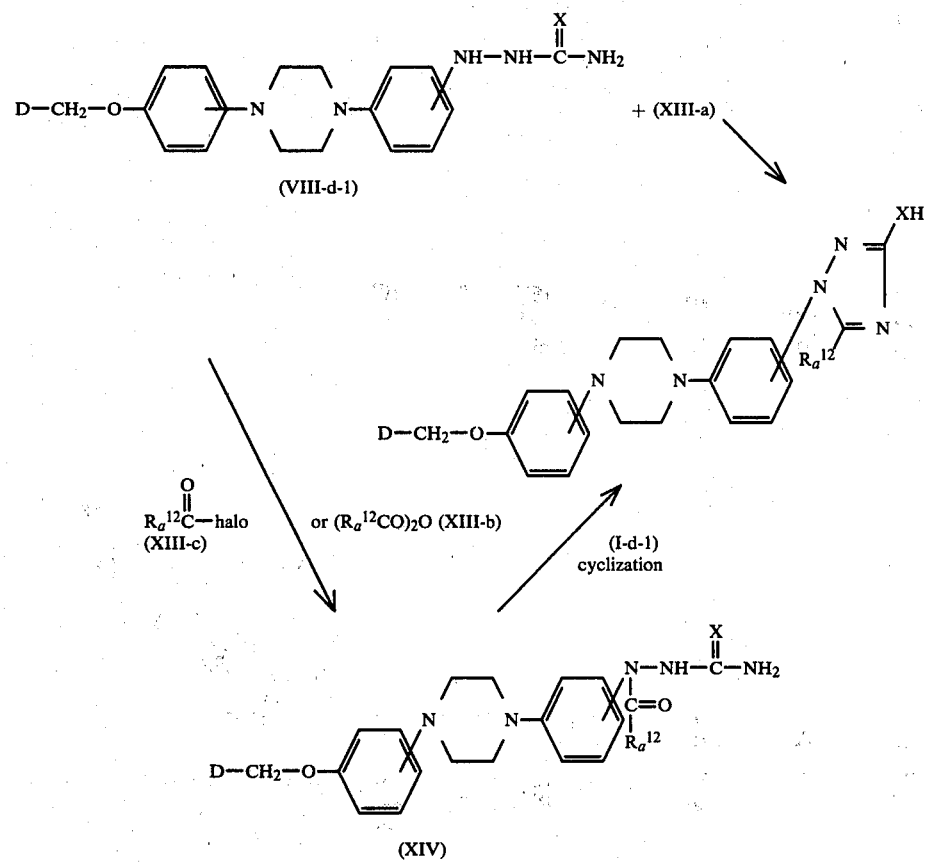

The compounds of formula (I) wherein Y is the radical (d), wherein $R^{11}$ represents XH, X being O or S, and wherein $R^{12}$ is hydrogen, lower alkyl or aryl-lower alkyl, said $R^{12}$ being represented by $R^{12}_a$ and said compounds by the formula (I-d-1), can be prepared by cyclizing a hydrazinecarbothioamide or a hydrazinecarboxamide of formula (VIII-d-1) with an appropriate carboxylic acid of the formula

(XIII)

or a functional derivative thereof such as, for example, an acyl halide, an ester, or preferably an imidamide of the formula

(XIII-a)

The reaction is conveniently carried out by stirring and heating the reactants together in an appropriate organic solvent, e.g., a lower alkanol such as, for example, 2-propanol, butanol and the like.

The intermediates of formula (VIII-d-1), used as starting materials herein, may be prepared by the reaction of an alkali metal isothiocyanate, e.g., potassium isothiocyanate, with the corresponding hydrazine derivative of formula (VIII-b).

Still another method of preparing the compounds of formula (I-d-1) is by reacting a hydrazine hydrochloride of formula (VIII-b) with a compound of formula (XIII-d) wherein X is O or S, in N,N-diethylethanamine, washing the reaction mixture with water, evaporating off the solvent and thereafter stirring and heating the residue in a mixture of dichloromethane and ethanol in the presence of alkali.

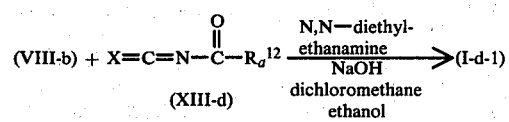

The compounds of formula (I) wherein Y stands for the radical (d) wherein $R^{12}$ is $R^{12}_a$ and wherein $R^{11}$ is hydrogen, said compounds being represented by the formula (I-d-2), can easily be prepared by desulfurating a corresponding compound of formula (I-d-1), wherein $R^{11}$ is SH, said compounds being represented by the formula (I-d-1-a) following the same procedure as for the desulfuration of (I-c-1) to prepare (I-c-2).

The compounds of formula (I) wherein Y stands for the radical (d) wherein $R^{12}$ is $R^{12}_a$ and wherein $R^{11}$ is lower alkylthio or aryl-lower alkylthio, said compounds being represented by the formula (I-d-3), can be obtained by S-alkylating a compound of formula (I-d-1-a) with a reactive ester of formula (XV-a), wherein W has the previously defined meaning and wherein $R^{11}_a$ stands for lower alkyl or aryl-lower alkyl, following the same procedure as for the preparation of (I-c-3) starting from (I-c-1) and (XII). Following the same desulfurating procedure as described hereinabove, the compounds of formula (I-c-3) may be converted into the compounds of formula (I-c-1).

The foregoing reactions are schematically illustrated as follows:

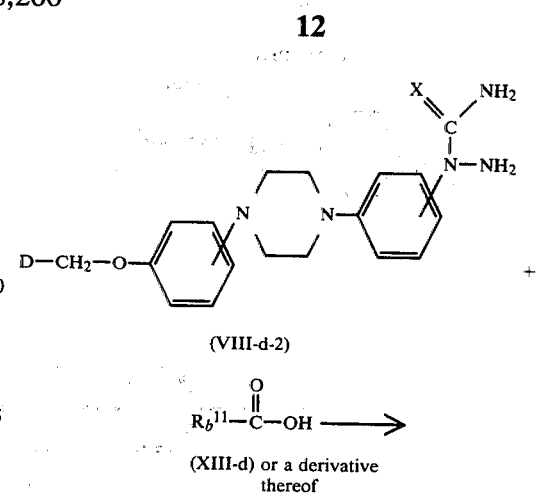

(VIII-d-2)

+

$R_b^{11}-\overset{O}{\underset{\|}{C}}-OH \longrightarrow$ (XIII-d) or a derivative thereof

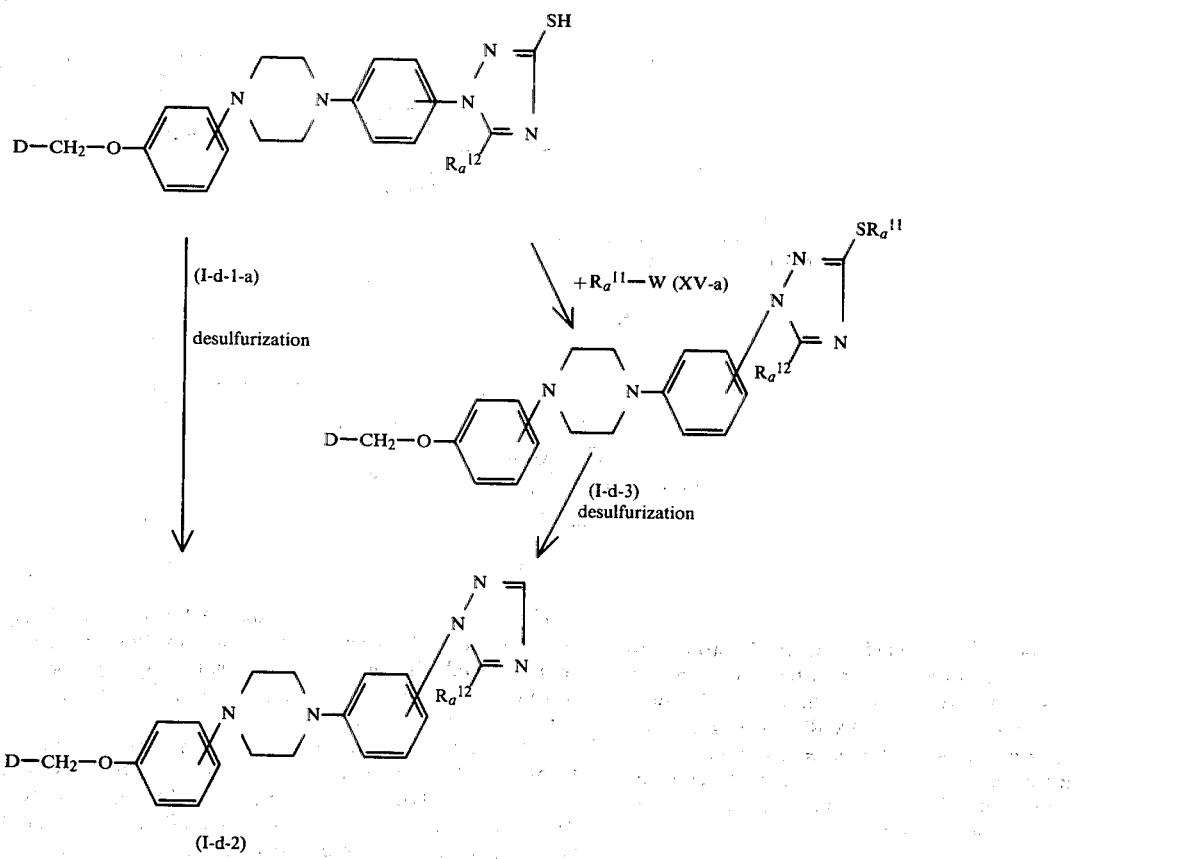

The compounds of formula (I) wherein $R^{12}$ is XH, X being O or S, and wherein $R^{11}$ is hydrogen, lower alkyl or aryl-lower alkyl, said $R^{11}$ being represented by $R^{11}_b$ and said compounds by the formula (I-d-4), may be prepared by cyclizing an appropriate (aminocarbonyl)- or (aminothiocarbonyl)hydrazine of formula (VIII-d-2) with an appropriate carboxylic acid (XIII-d) or a functional derivative thereof, e.g., an acyl halide, an ester or, preferably an imidamide.

Said reaction is preferably carried out in the presence of an appropriate organic solvent, e.g., a lower alkanol such as, for example, 2-propanol, butanol and the like.

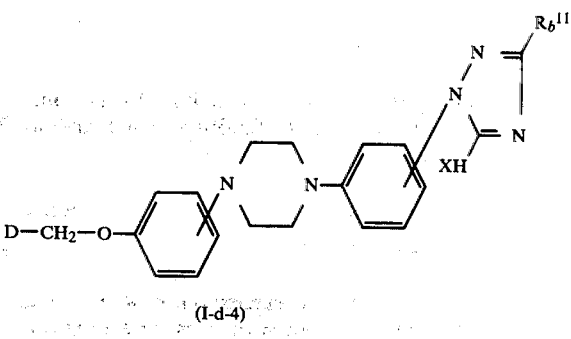

(I-d-4)

The compounds of formula (I) wherein Y represents the radical (d) wherein $R^{12}$ is hydrogen and wherein $R^{11}$ has the meaning of $R^{11}{}_b$, said compounds being represented by the formula (I-d-5), may be prepared by desulfurating a compound of formula (I-d-4) wherein X is S, (I-d-4-a), e.g., by treating the latter with Raney-nickel or with diluted nitric acid.

The compounds of formula (I) wherein Y represents the radical (d) wherein $R^{12}$ is lower alkylthio or aryl-lower alkylthio and wherein $R^{11}$ has the meaning of $R^{11}{}_b$; said compounds being represented by the formula (I-d-6), may be prepared by S-alkylating a compound of formula (I-d-4-a) with a reactive ester of formula (XV-b), wherein W is as previously described and wherein $R^{12}{}_b$ is lower alkyl or aryl-lower alkyl, following the previously described procedure for the preparation of (I-c-3) starting from (I-c-1) and (XII).

Following the desulfurating procedure described hereinabove, the compounds of formula (I-d-6) may in turn be converted into the compounds of formula (I-d-5).

The foregoing reactions are schematically illustrated as follows:

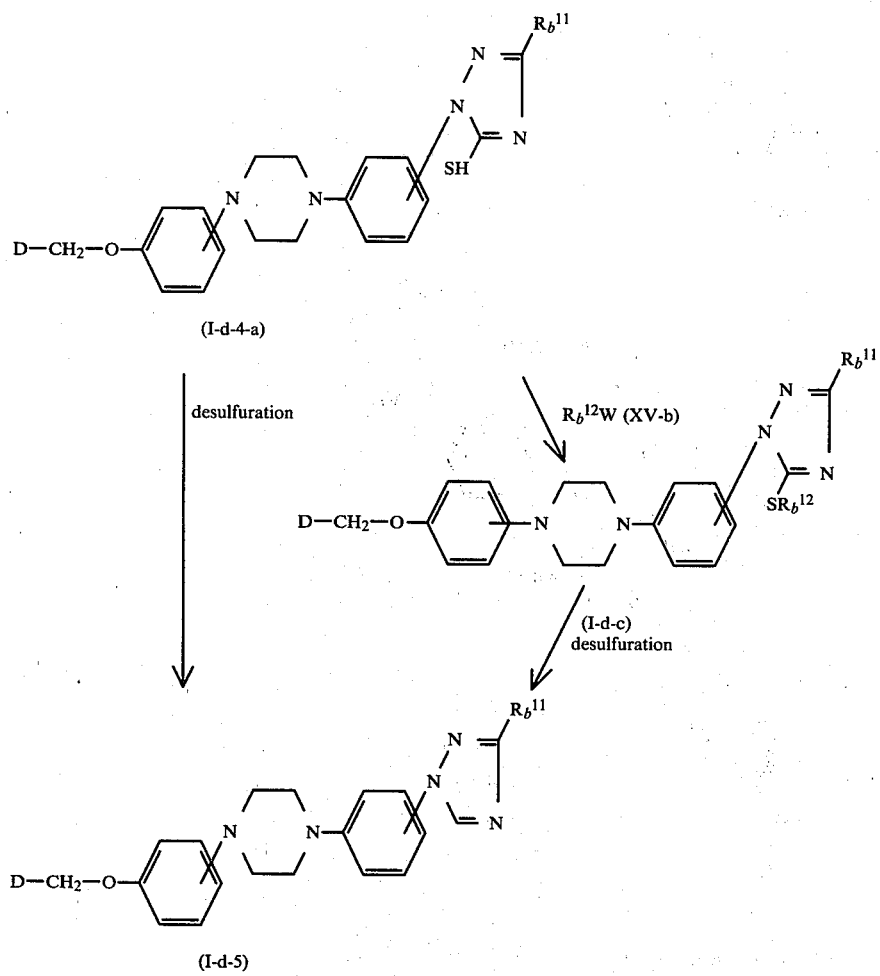

The compounds of formula (I) wherein Y stands for a radical of formula (e) wherein $R^{14}$ has the previously defined meaning and wherein $R^{13}$ stands for mercapto or hydroxy, said $R^{13}$ being represented by XH, wherein X is O or S and said compounds by the formula (I-e-1), can be derived from an intermediate of formula (VIII-e) by cyclizing the latter with an appropriate imidamide of formula (XVI) or an acid addition salt thereof.

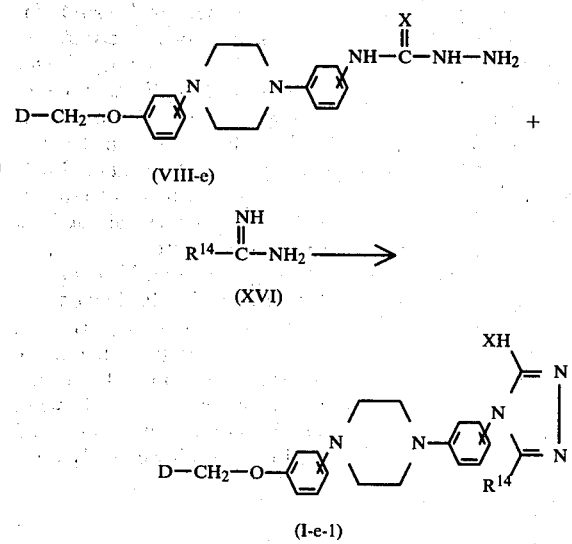

The cyclization may be carried out according to methodologies known in the art, for example, by mixing and melting the reactants together, if desired, in the presence of an appropriate reaction-inert organic solvent having a relatively high boiling point such as, for example, 1,1'-oxybis(2-methoxyethane).

The compounds of formula (I) wherein Y stands for the radical (e) wherein $R^{14}$ is as previously defined and wherein $R^{13}$ stands for lower alkylthio or aryl-lower alkylthio, said $R^{13}$ being represented by $SR^{13}_a$, wherein $R^{13}_a$ is lower alkyl or aryl-lower alkyl, said compounds being represented by the formula (I-e-3), can be prepared by S-alkylating a compound of formula (I-e-1) wherein $R^{13}$ is —SH, (I-e-1-a), with a reactive ester of formula (XVII), wherein W has the previously defined meaning, following art-known procedures.

The compounds of formula (I) wherein Y stands for the radical (e) wherein $R^{14}$ is as previously defined and wherein $R^{13}$ stands for hydrogen, said compounds being represented by the formula (I-e-2), can be prepared by desulfurating a corresponding compound of formula (I-e-1-a) or a compound of formula (I-e-3), following standard desulfuration reactions as previously described herein. The foregoing reactions are schematically illustrated as follows:

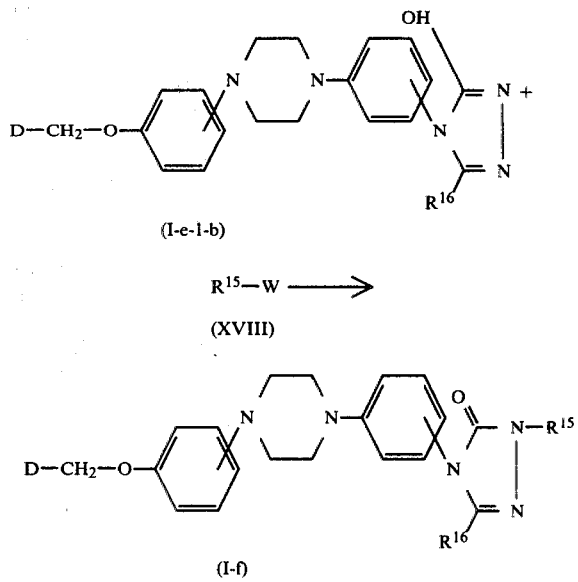

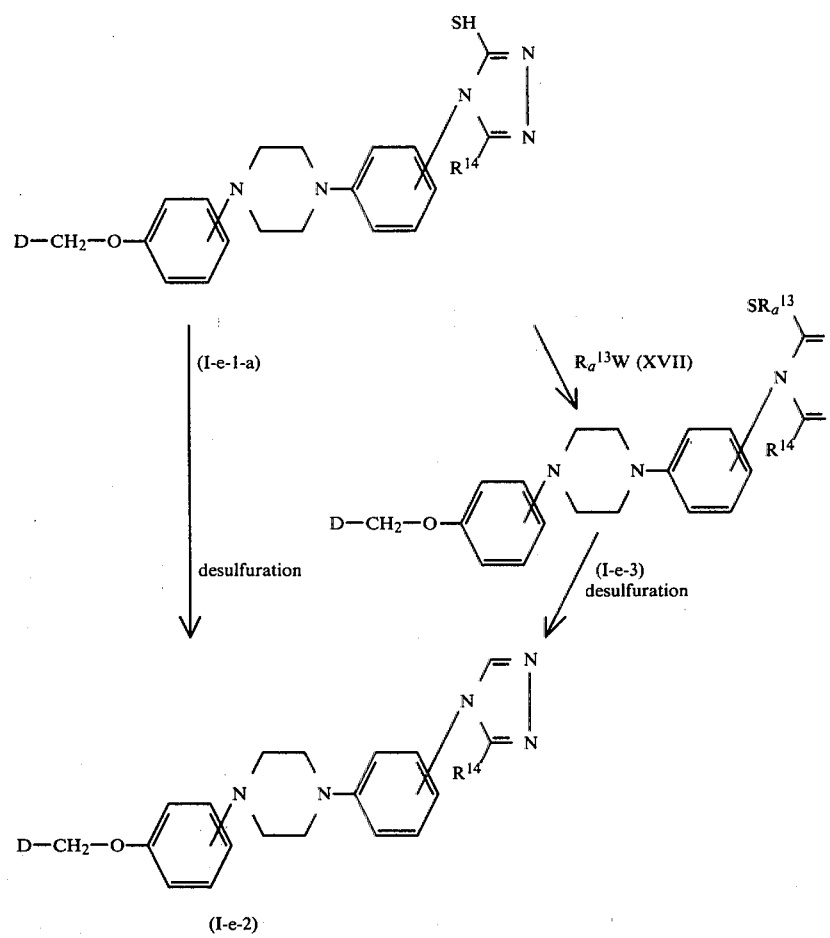

The compounds of formula (I) wherein Y represents a radical (f) wherein $R^{15}$ and $R^{16}$ have the previously defined meaning, said compounds being represented by the formula (I-f), can be derived from an appropriate compound of formula (I-e-1), wherein $R^{13}$ stands for OH, (I-e-1-b), by N-alkylating the latter with an appropriate reactive ester of formula (XVIII), wherein W and $R^{15}$ have the previously defined meanings.

Said N-alkylation may be carried out in the usual manner, e.g., by stirring and heating the reactants together in an appropriate organic solvent such as, for example, dimethylsulfoxide and the like, in the presence of an appropriate base such as, for example, an alkali metal hydride or carbonate.

The compounds of formula (I) wherein Y stands for the radical (g) wherein $R^{17}$ is as previously defined, but other than mercapto, said compounds being represented by the formula (I-g-1) and said $R^{17}$ by $R^{17}_a$, can generally be derived from an intermediate of formula (VIII-a) by cyclizing the latter with an azide, preferably an alkali metal azide, e.g., sodium azide, and an appropriate 1,1',1''-tri(lower alkyloxy)-alkane of formula (XIX) in an appropriate acidic medium, e.g., acetic acid, preferably under heating.

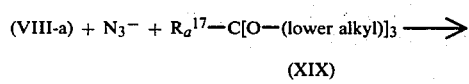

(XIX)

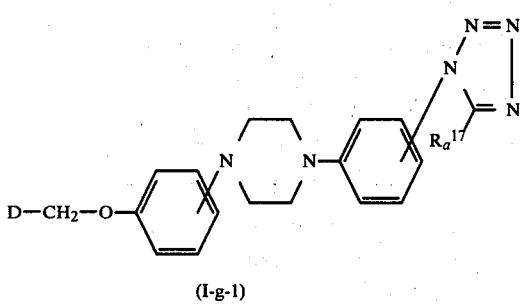

(I-g-1)

The compounds of formula (I), wherein Y stands for the radical (g) wherein $R^{17}$ stands for mercapto, said compounds being represented by the formula (I-g-2) can be obtained by cyclizing an isothiocyanate of formula (VIII-c) with an appropriate azide, preferably sodium azide, in an appropriate organic solvent, e.g., a lower alkanol such as methanol, ethanol, 2-propanol and the like, in the presence of alkali.

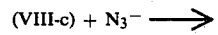

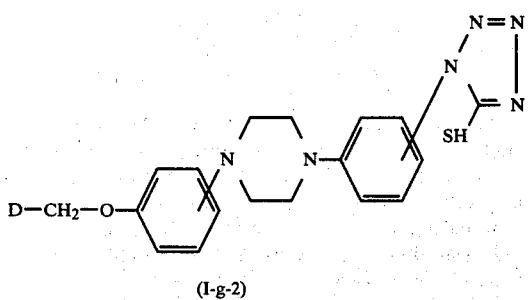

(I-g-2)

Said cyclization reaction may also be carried out by stirring (VIII-c) with an azide in the presence of an appropriate quaternary ammonium salt, preferably N,N,N-triethylbenzenemethanaminium chloride, in a suitable solvent system such as, for example, water, preferably in admixture with an appropriate organic solvent such as, for example, 1,4-dioxane, to better solubilize the reactants. The compounds of formula (I-g) wherein $R^{17}$ is hydrogen, (I-g-3), may be prepared by desulfurating a compound of formula (I-g-2) following art known procedures.

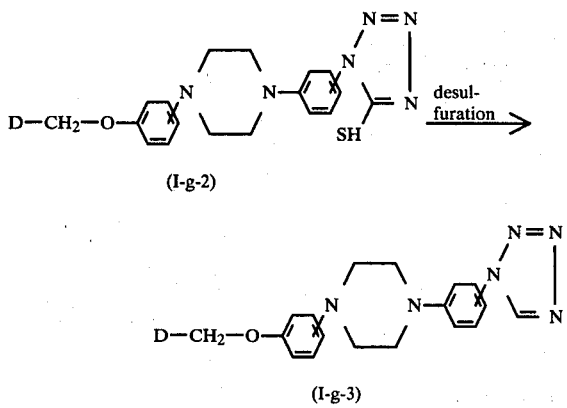

The imidazole- and triazole-derivatives of formula (I), obtained in base form in the foregoing preparations, may be converted to their therapeutically useful acid addition salts by reaction with an appropriate acid, as, for example, an inorganic acid such as hydrohalic acid, i.e., hydrochloric, hydrobromic or hydroiodic acid; sulfuric, nitric or thiocyanic acid; a phosphoric acid; an organic acid such as acetic, propanoic, hydroxyacetic, 2-hydroxypropanoic, 2-oxopropanoic, ethanedioic, propanedioic, 1,4-butanedioic, (Z)-2-butenedioic, (E)-2-butenedioic, 2-hydroxy-1,4-butanedioic, 2,3-dihydroxy-1,4-butanedioic, 2-hydroxy-1,2,3-propanetricarboxylic, benzoic, 3-phenyl-2-propenoic, α-hydroxybenzeneacetic, methanesulfonic, ethanesulfonic, 2-hydroxyethanesulfonic, 4-methylbenzenesulfonic, 2-hydroxybenzoic, 4-amino-2-hydroxybenzoic, 2-phenoxybenzoic or 2-acetyloxybenzoic acid. The salts are in turn converted to the corresponding free bases in the usual manner, e.g., by reaction with alkali such as sodium or potassium hydroxide.

A number of the intermediates and starting materials used in the foregoing preparations are known compounds, others may be prepared according to art-known methodologies of preparing similar compounds and some of them are novel and consequently their preparation will be described hereafter.

The intermediates of formula (III), wherein Y' has the previously defined meaning, can generally be prepared from the corresponding methoxy-substituted compounds of formula (XX) by converting the methoxy group of the latter into a hydroxy group by acid hydrolysis using a strong non-oxidizing mineral acid such as, for example, hydrobromic acid in glacial acetic acid.

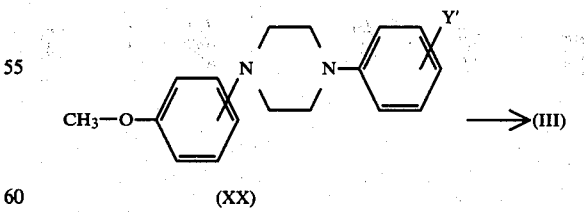

The intermediates of formula (XX), used as starting materials herein, can be obtained by cyclizing a N,N-bis(2-haloethyl)-4-methoxybenzenamine of formula (XXI), with an appropriate benzenamine of formula (XXII), wherein Y' has the previously defined meaning, following the same procedure as described for the preparation of (I) starting from (IV) and (V).

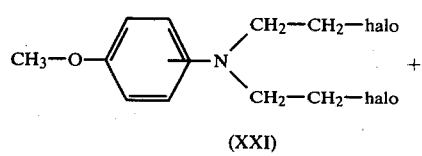

(XXI)

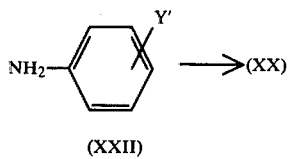

(XXII)

The preparation of the compounds of formula (XXI) is described in J. Chem. Soc., 1949, 183–191.

The intermediates of formula (XX) can alternatively be prepared by cyclizing an appropriate intermediate of formula (XXIII), wherein A is an amine group or a derivative thereof, with an appropriate cyclizing agent and, if desired, introducing appropriate substituents into the thus obtained heterocyclic compounds, following the previously described methods for the preparation of compounds (I) starting from (VIII).

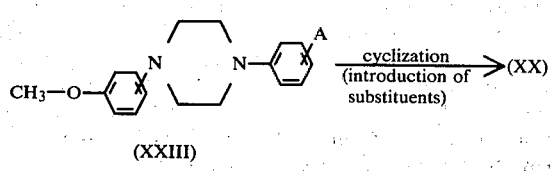

(XXIII)

The intermediates of formula (XXIII) wherein A stands for an amino group, (XXIII-a), can be prepared by N-alkylating a compound of formula (XXIV) with an appropriate chloro-nitrobenzene (XXV), following standard N-alkylating procedures, and subsequently reducing the thus obtained nitro-compound (XXVI), e.g., by catalytic hydrogenation in a relatively polar solvent, such as, for example, methanol, in the presence of an appropriate catalyst, e.g., palladium on charcoal.

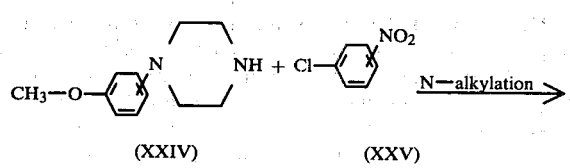

(XXIV)    (XXV)

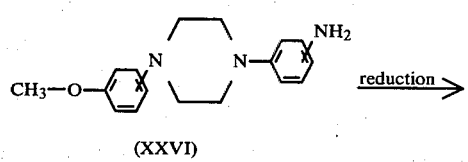

(XXVI)

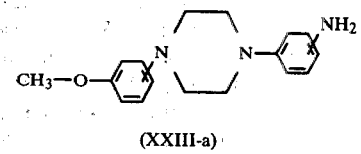

(XXIII-a)

The intermediates of formula (XXIII), wherein A represents an isothiocyanate group, (XXIII-b), can be derived from an appropriate compound of formula (XXIII-a), by treating the latter with carbon disulfide in the presence of dicyclohexylcarbodiimide, preferably in the presence of an appropriate organic solvent such as, for example, pyridine.

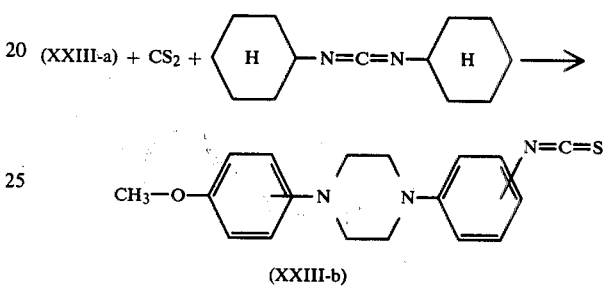

(XXIII-b)

The intermediates of formula (XXIII), wherein A stands for a hydrazinecarbothioamide group, (XXIII-c-1), can be derived from a compound of formula (XXIII-b), by stirring and heating the latter with hydrazine hydrate in the presence of an appropriate solvent such as, for example, 1,4-dioxane and the like.

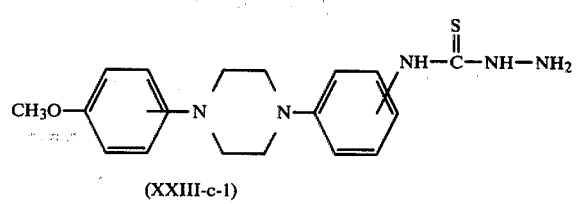

(XXIII-c-1)

The intermediates of formula (XXIII), wherein A stands for a hydrazinecarbonamide group, (XXIII-c-2), can be derived from a compound of formula (XXIII-a), by stirring and heating the latter with phenylcarbonohalogenidate in an appropriate solvent, e.g., dichloromethane, in the presence of an appropriate base such as, for example, pyridine and the like, and subsequently reacting the thus obtained (XXIII-d) with hydrazine hydrate in the presence of an appropriate solvent, e.g., 1,4-dioxane and the like.

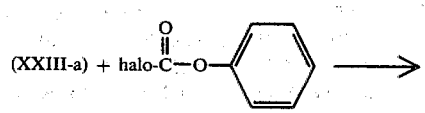

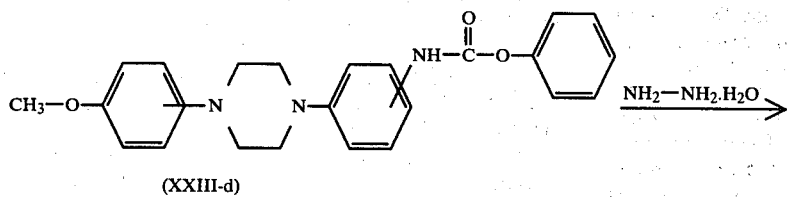

(XXIII-d)

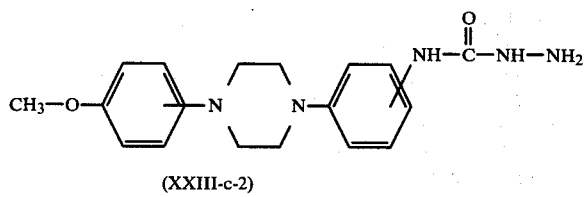

(XXIII-c-2)

The intermediates of formula (IV) can be prepared by O-alkylating a 4-amino-phenol of formula (XXVI) with a reactive ester of formula (II), following the same procedure as previously described herein for the preparation of (I'), and subsequently reacting the thus obtained compounds of formula (XXVII) with an appropriate dihaloethane, following the method described in J. Chem. Soc., 1949, 183–191.

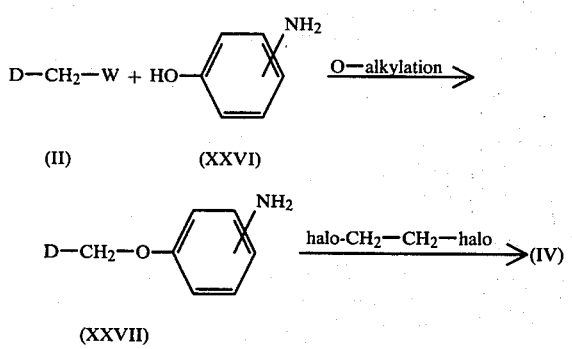

The intermediates of formula (V) and the starting materials of formula (XXII) can generally be prepared by reducing a corresponding nitro compound of formula (XXVIII), respectively (XXVIII-a), e.g., by catalytic hydrogenation in a relatively polar solvent such as, for example, an alkanol, in the presence of an appropriate catalyst, e.g., platinum on charcoal.

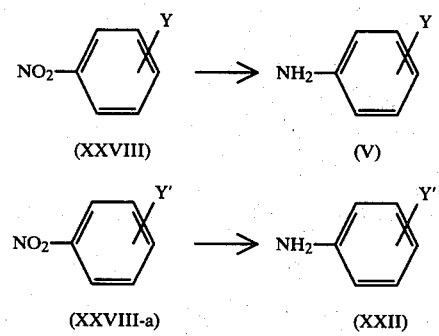

The starting materials of formula (XXVIII), respectively (XXVIII-a), can be prepared starting from appropriate precursors, following art-known procedures as previously described herein for the preparation of compounds of formula (I) starting from (VIII) and an appropriate cyclizing agent.

The intermediates of formula (VI) can be obtained by O-alkylating an appropriate compound of formula (XXIX) with a reactive ester of formula (II), following standard O-alkylation procedures.

D—CH$_2$—W +

(II)

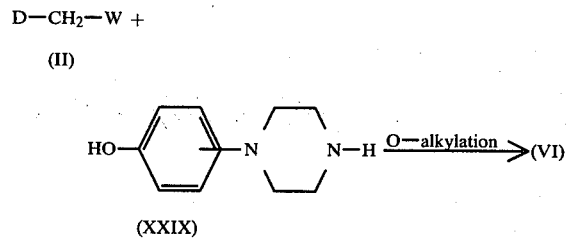

(XXIX)

Starting materials of formula (II) wherein Q stands for CH and methods of preparing the same are described in Belg. Pat. No. 837,831. In general the reactive esters of formula (II) can be prepared along the following sequence of reactions.

An appropriate I-Ar-2-bromoethanone of formula (XXX) is subjected to a ketalization reaction with 1,2,3-propanetriol following methodologies analogous to those described in Synthesis, 1974, (I), 23.

In a preferred manner of carrying out the reaction both reactants are refluxed together for several hours with azeotropic water removal in an appropriate organic solvent, preferably in the presence of a simple alcohol, such as, for example, ethanol, propanol, butanol, pentanol and the like, and in the presence of an appropriate strong acid such as 4-methylbenzenesulfonic acid. Suitable organic solvents are, for example, aromatic hydrocarbons, such as benzene, methylbenzene, dimethylbenzene and the like and saturated hydrocarbons, such as cyclohexane.

The thus obtained dioxolane (XXXI) is then reacted with benzoyl chloride to obtain a benzoate of the formula (XXXI) and the latter is subsequently reacted with 1H-imidazole or 1H-1,2,4-triazole. Said reaction is preferably carried out by stirring and heating the reactants together in a suitable organic solvent, e.g., N,N-dimethylformamide, in the presence of an appropriate strong metal base, e.g., sodium methanolate, to obtain an intermediate of the formula (XXXIII). The desired reactive esters of formula (II) are then conveniently prepared by first hydrolyzing (XXXIV) in alkaline medium and thereafter converting the hydroxy group of the thus obtained (XXXV) into a reactive ester thereof according to methodologies generally known in the art. For example, methanesulfonates and 4-methylbenzenesulfonates are conveniently prepared by the reaction of the alcohol with methanesulfonyl chloride or 4-methylbenzenesulfonyl chloride and halides may be prepared by the reaction of the alcohol with an appropriate halogenating agent such as, for example, thionyl chloride, phosphor pentachloride, phosphor pentabromide, phosphoryl chloride and the like. When the reactive ester is an iodide, it is preferably prepared from the corresponding chloride or bromide by the replacement of that halogen with iodine.

The foregoing reactions may be illustrated as follows:

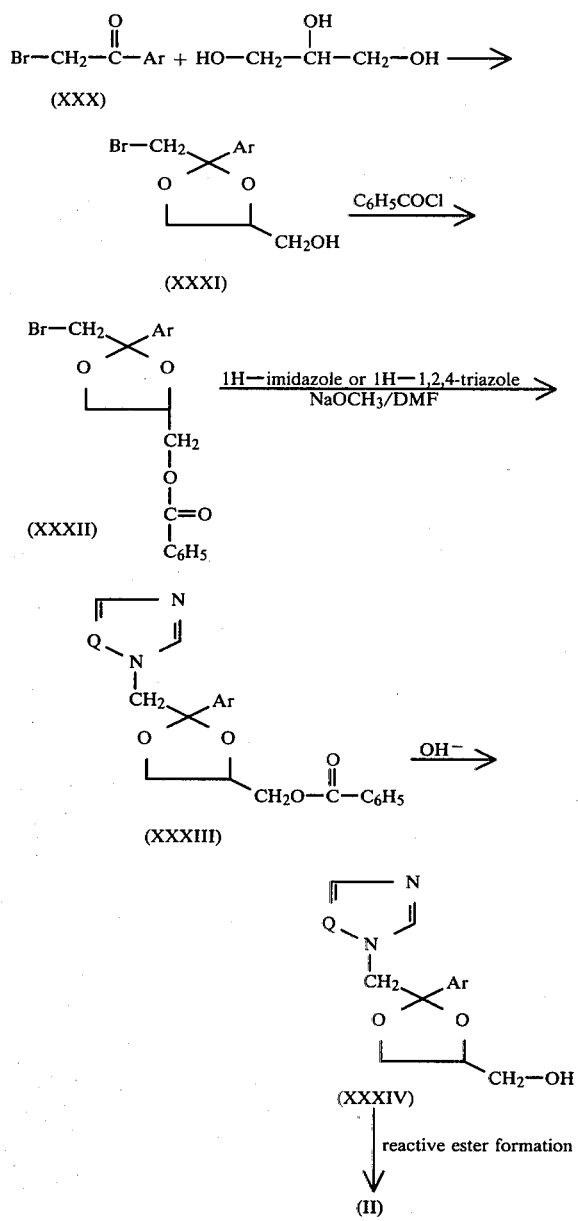

From formula (I) it is evident that the compounds of this invention have at least two asymmetric carbon atoms in their structures, namely those located in the 2- and 4-position of the dioxolane nucleus, and consequently they can exist under different stereochemically isomeric forms. The stereochemically isomeric forms of (I) and the pharmaceutically acceptable acid addition salts thereof are intended to be within the scope of this invention.

The diastereomeric racemates of (I), denoted as cis and trans forms respectively, according to the rules described in C.A., 76, Index Guide, Section IV, p. 85 (1972), may be obtained separately by conventional methods. Appropriate methods which may advantageously be employed therefore include, for example, selective crystallization and chromatographic separation, e.g., column-chromatography.

Since the stereochemical configuration is already fixed in a number of intermediate compounds, e.g., in intermediates of the formulas (II), (IV), (VI) and (VIII) it is also possible to separate cis and trans forms at this or even an earlier stage, whereupon the corresponding forms of (I) may be derived therefrom in the previously indicated manner. The separation of cis and trans forms of such intermediates may be performed by conventional methods as described hereabove for the separation of cis and trans forms of the compounds (I).

It is evident that the cis and trans diastereomeric racemates may be further resolved into their optical isomers, cis(+), cis(−), trans(+) and trans(−) by the application of methodologies known to those skilled in the art.

The compounds of formula (I) and the pharmaceutically acceptable acid addition salts thereof are useful agents in combatting fungi and bacteria. For example, said compounds and acid addition salts thereof were found to be highly active against a wide variety of fungi such as, for example, *Microsporum canis, Ctenomyces mentagrophytes, Trichophyton rubrum, Phialophora verrucosa, Cryptococcus neoformans, Candida tropicalis, Candida albicans, Mucor species, Aspergillus fumigatus, Sporotricum schenckii* and *Saprolegnia species*, and against bacteria such as, for example, *Erysipelotrix insidiosa*, Staphylococci such as *Staphylococcus hemolyticus* and Streptococci such as *Streptococcus pyrogenes*. In view of their potent, local as well as systemic, antimicrobial activity the compounds of this invention constitute useful tools for the destruction or prevention of the growth of fungi and bacteria and more particularly they can effectively be used in the treatment of subjects suffering from such microorganisms.

The strong antimicrobial activity of the compounds (I) is clearly evidenced by the data obtained in the following experiments, which data are only given to illustrate the useful antimicrobial properties of all the compounds (I) and not to limit the invention either with respect to the scope of susceptible microorganisms nor with respect to the scope of formula (I).

Experiment A: Activity of compounds (I) against vaginal candidosis in rats

Female Wistar rats of ±100 g body weight are used. They are ovariectomized and hysterectomized and after three weeks of recovery, 100 µg of oestradiol undecylate in sesame oil is given subcutaneously once a week for 3 consecutive weeks. The thus induced pseudo-oestrus is controlled by microscopic examination of vaginal smears. Food and water are left available ad libitum. The rats are infected intravaginally with $8.10^5$ cells of *Candida albicans*, grown on Sabouraud broth for 48 hours at 37° C. and diluted with saline. The data of infection varies from day +25 to day +32 after surgical intervention, depending on the appearance of signs of induced pseudo-oestrus.

The drugs under investigation are administered orally once a day for two days starting from the day of infection. For each experiment there are placebo treated controls. The results are assessed by taking vaginal smears with sterile swabs on several days after the infection. The swabs are put into Sabouraud broth in petri-dishes and incubated for 48 hours at 37° C. If no growth of Candida albicans occurs, i.e., when the animals are negative at the end of the experiment, this is due to drug administration because it never happens in placebo-treated controls.

The table below gives the lowest oral dose of the drug under investigation which is found active at the 14th day after infection.

Experiment B: Activity of compounds (I) against crop candidosis in turkeys

Turkeys of 14 days old are infected in the crop with $4.10^6$ Candida albicans cells, grown on Sabouraud broth for 48 hours at 37° C. and diluted with saline. The volume of the inoculum is 1 ml. The drugs under investigation are premixed in 500 mg of lacton and thereafter admixed in 1000 g of meal without any additives. The concentration of the drug under investigation in the meal is expressed in mg/kg.

The animals are given the medicated feed for 13 consecutive days starting on the day of infection. At the end of the experiment all animals are sacrificed. At autopsy the crops are removed, emptied and grinded in an ultra-turrax mixer in 15 ml of sterile saline. Colony counting is done on Sabouraud agar and the results given in the table represent the $ED_{50}$, i.e., the dose of the drug whereby the crops of 50% of the animals are completely negative for Candida albicans.

The compounds listed in the table are intended to illustrate and not to limit the scope of the present invention.

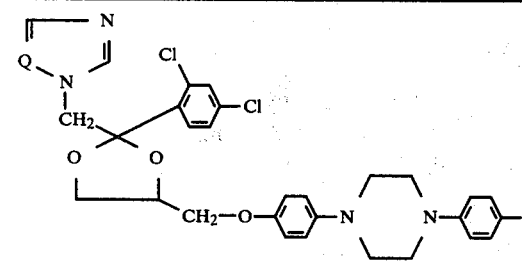

| Y | Q | Vaginal candidosis in rats: lowest effective dose in mg/kg orally | Crop candidosis in turkeys: $ED_{50}$ in mg/kg in feed. |
|---|---|---|---|
| −N(N=) pyrazole | CH | 2.5 | — |
| −N(N=) pyrazole | N | 2.5 | — |
| −N(=N) imidazole | CH | 1.25 | — |
| −N(=N) imidazole | N | 1.25 | 16 |
| −N(N=N) triazole | CH | 0.63 | 16 |
| −N(N=N) triazole | N | 0.63 | — |
| −N(N=N)−SCH₃ | CH | 2.5 | — |
| −N(N=N)−SCH₃ | N | 1.25 | 31 |
| −N(N=)(CH₃)−SCH₃ | CH | 2.5 | — |
| −N(N=)(CH₃)−SCH₃ | N | ≦0.63 | — |

-continued

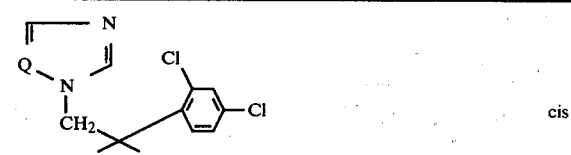

cis

| Y | Q | Vaginal candidosis in rats: lowest effective dose in mg/kg orally | Crop candidosis in turkeys: ED$_{50}$ in mg/kg in feed. |
|---|---|---|---|
| -N(=N)-C(SCH$_3$)=N, CH$_3$ (triazole with SCH$_3$ and CH$_3$) | N | 2.5 | — |
| -N(-N=)-C(=N)SCH$_3$ (triazole) | N | 2.5 | — |
| -N-N=CH, C(CH$_3$)=N (triazole with CH$_3$) | N | 0.63 | — |
| -N... SCH$_3$, CH$_3$ triazole | CH | — | 31 |
| -N... CH$_3$, CH$_3$, O (triazolinone) | CH | 0.63 | 16 |
| -N... CH$_3$, CH$_3$, O (triazolinone) | N | ≦0.63 | 16 |
| -N-N=N, N=CH (tetrazole) | N | <2.5 | — |

-continued

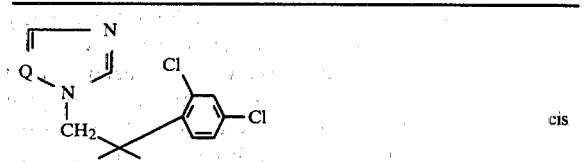

cis

| Y | Q | Vaginal candidosis in rats: lowest effective dose in mg/kg orally | Crop candidosis in turkeys: ED$_{50}$ in mg/kg in feed. |
|---|---|---|---|
| -N-C(=O)-N(CH$_3$)-N=CH (triazolinone) | N | ≧0.63 | — |
| -N-C(=O)-N(CH$_3$)-N=CH | CH | 1.0 | 16 |
| -N-C(=O)-N(C$_2$H$_5$)-N=CH | CH | 1.25 | 31 |
| -N-C(=O)-N(nC$_3$H$_7$)-N=C(CH$_3$) | CH | 0.63 | — |
| -N-C(=O)-N(C$_2$H$_5$)-N=C(CH$_3$) | N | <0.63 | — |
| -N-C(=O)-N(nC$_3$H$_7$)-N=C(CH$_3$) | N | 0.5 | — |
| -N-C(=O)-N(C$_2$H$_5$)-N=CH | N | ≧0.16 | — |

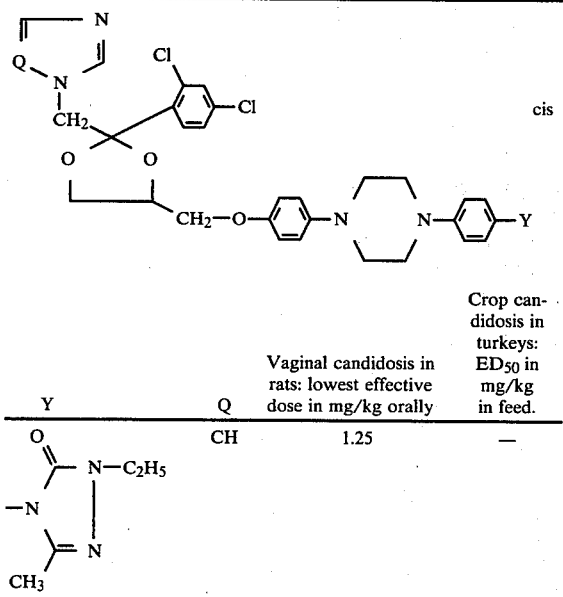

| Y | Q | Vaginal candidosis in rats: lowest effective dose in mg/kg orally | Crop can- didosis in turkeys: ED$_{50}$ in mg/kg in feed. |
|---|---|---|---|
| O=⟨N—C$_2$H$_5$⟩—N〉=N / CH$_3$ | CH | 1.25 | — |

In view of their antifungal and antibacterial properties this invention provides valuable compositions comprising the subject compounds of formula (I) or acid addition salts thereof as the active ingredient in a solvent or a solid, semi-solid or liquid diluent or carrier, and, in addition, it provides an effective method of combatting fungal or bacterial growth by use of an effective antifungal or antibacterial amount of such compounds (I) or salts thereof. Antifungal and antibacterial compositions comprising an effective amount of an active compound (I), either alone or in combination with other active therapeutic ingredients, in admixture with suitable carriers may be readily prepared according to conventional pharmaceutical techniques for the usual routes of administration.

Preferred compositions are in dosage unit form, comprising per dosage unit an effective quantity of the active ingredient in admixture with suitable carriers. Although the amount of the active ingredient per unit dosage may vary within rather wide limits, dosage units comprising from about 50 to about 500 mg and more particularly from about 100 to about 250 mg of the active ingredient are preferred.

The following examples are intended to illustrate and not to limit the scope of the present invention.

Unless otherwise stated all parts therein are by weight.

(A) PREPARATION OF INTERMEDIATES

Example I

A mixture of 13.4 parts of 1-(4-methoxyphenyl)piperazine dihydrochloride, 7.9 parts of 1-chloro-4-nitrobenzene, 10 parts of potassium carbonate and 90 parts of N,N-dimethylformamide is stirred and refluxed overnight. The reaction mixture is diluted with water and the product is extracted twice with trichloromethane. The combined extracts are dried, filtered and evaporated. The residue is triturated in 4-methyl-2-pentanone. The product is filtered off and crystallized from 1,4-dioxane, yielding 10.5 parts (67%) of 1-(4-methoxyphenyl)-4-(4-nitrophenyl)piperazine; mp. 195.1° C.

A mixture of 12 parts of 1-(4-methoxyphenyl)-4-(4-nitrophenyl)piperazine, 200 parts of methanol and 225 parts of tetrahydrofuran is hydrogenated at normal pressure and at room temperature with 2 parts of palladium-on-charcoal catalyst 10%. After the calculated amount of hydrogen is taken up, the catalyst is filtered off and washed with N,N-dimethylacetamide. The filtrate is poured onto water. The precipitated product is filtered off and crystallized from 1-butanol, yielding 8 parts (74%) of 4-[4-(4-methoxyphenyl)-1-piperazinyl]-benzenamine; mp. 191.8° C.

Example II

To a stirred and cooled (ice-bath) mixture of 5 parts of N,N'-methanetetraylbis[cyclohexanamine], 25.2 parts of carbon disulfide and 40 parts of pyridine are added 6 parts of 4-[4-(4-methoxyphenyl)-1-piperazinyl]benzenamine and the whole is stirred first for 1 hour in an ice-bath and further for 2 hours at room temperature. 35 Parts of 2,2'-oxybispropane are added and the whole is stirred for 30 minutes. The precipitated product is filtered off and crystallized from 4-methyl-2-pentanone. The product is filtered off again and recrystallized from 1,4-dioxane, yielding 2.45 parts of 1-(4-isothiocyanato-phenyl)-4-(4-methoxyphenyl)piperazine; mp. 180.6° C.

A mixture of 47.8 parts of 1-(4-isothiocyanato-phenyl)-4-(4-methoxyphenyl)piperazine, 100 parts of hydrazine hydrate and 400 parts of 1,4-dioxane is stirred and refluxed for 1 hour. The reaction mixture is cooled and poured onto water. The precipitated product is filtered off, washed with water and with methanol and dried, yielding 46 parts (89%) of N-{4-[4-(4-methoxy-phenyl)-1-piperazinyl]phenyl}hydrazinecarbothioamide.

EXAMPLE III

A mixture of 23 parts of N-{4-(4-methoxyphenyl)-1-piperazinyl]phenyl}hydrazinecarbothioamide, 23 parts of methanimidamide acetate and 80 parts of 1-butanol is stirred and refluxed for 1 hour. The reaction mixture is cooled and poured onto water. 2,2'-oxybispropane is added. The precipitated product is filtered off, washed with water and with methanol and crystallized from 1-butanol, yielding 17.7 parts of 4-{4-[4-(4-methoxy-phenyl)-1-piperazinyl]phenyl}-4H-1,2,4-triazole-3-thiol; mp. 231.9° C.

Following the same procedure and using an equivalent amount of ethanimidamide hydrochloride in place of the methanimidamide acetate used therein, there is obtained 4-{4-[4-(4-methoxyphenyl)-1-piperazinyl]-phenyl}-5-methyl-4H-1,2,4-triazole-3-thiol; mp. 260.3° C.

Example IV

A mixture of 9 parts of 4-{4-[4-(4-methoxyphenyl)-1-piperazinyl]phenyl}-4H-1,2,4-triazole-3-thiol, 2 parts of sodium hydroxide and 160 parts of methanol is stirred and warmed till all solid enters solution. Then there are added 3.3 parts of dimethyl sulfate and stirring is continued for 3 hours at room temperature. The reaction mixture is poured onto water. The precipitated product is filtered off and crystallized from 1-butanol, yielding 5.3 parts of 1-(4-methoxyphenyl)-4-{4-[3-(methylthio)-4H-1,2,4-triazol-4-yl]phenyl}piperazine; mp. 180° C.

In a similar manner there is prepared:
1-(4-methoxyphenyl)-4-{4-[3-methyl-5-(methylthio)-4H-1,2,4-triazol-4-yl]phenyl}piperazine dihydrochloride; mp. 210° C.

Example V

A mixture of 50 parts of 2-(4-nitrophenyl)hydrazinecarbothioamide and 270 parts of methylbenzene is distilled azeotropically to dry. Then there are added 26 parts of acetic acid anhydride and the whole is stirred and refluxed for 3 hours. The reaction mixture is cooled. The precipitated product is filtered off, washed with 2-propanol and crystallized from ethanol. It is filtered off again and dried at 100° C., yielding 31.5 parts of acetic acid, 2-(aminothioxomethyl)-1-(4-nitrophenyl)hydrazide; mp. 241.5° C.

Following the same acetylation-procedure and using equivalent amounts of the appropriate starting materials there are also prepared:
butanoic acid, 2-(aminothioxomethyl)-1-(4-nitrophenyl)hydrazide monohydrate; mp. 197.2° C.; and
propanoic acid, 2-(aminothioxomethyl)-1-(4-nitrophenyl)hydrazide; mp. 216.1° C.

Example VI

40 Parts of acetic acid, 2-(aminothioxomethyl)-1-(4-nitrophenyl)hydrazide are dissolved in a mixture of 10 parts of sodium hydroxide and 400 parts of water and the solution is stirred for 30 minutes at room temperature. The reaction mixture is acidified with concentrated hydrochloric acid. The precipitated product is filtered off, washed with water and with 2-propanol and crystallized from 1,4-dioxane, yielding 22.4 parts of 5-methyl-1-(4-nitrophenyl)-1H-1,2,4-triazole-3-thiol; mp. 202.1° C.

In a similar manner there are also prepared:
1-(4-nitrophenyl)-5-propyl-1H-1,2,4-triazole-3-thiol; mp. 190.7° C.; and
5-ethyl-1-(4-nitrophenyl)-1H-1,2,4-triazole-3-thiol; mp. 206.1° C.

Example VII

To 80 parts of methanol are added 4.7 parts of 5-methyl-1-(4-nitrophenyl)-1H-1,2,4-triazole-3-thiol and 1.2 parts of sodium hydroxide and the whole is stirred till all solid enters solution. Then there are added 2.66 parts of dimethyl sulfate and stirring is continued for 1 hour at room temperature. 100 Parts of water are added. The precipitated product is filtered off, washed with water, dried, and crystallized from 2,2'-oxybispropane, yielding 3.3 parts (66%) of 5-methyl-3-(methylthio)-1-(4-nitrophenyl)-1H-1,2,4-triazole; mp. 121°–125° C.

Following the same S-methylation procedure and using equivalent amounts of the appropriate starting materials there are also prepared:
5-ethyl-3-(methylthio)-1-(4-nitrophenyl)-1H-1,2,4-triazole; mp. 77.8° C.; and
3-(methylthio)-1-(4-nitrophenyl)-1H-1,2,4-triazole; mp. 140° C.

Example VIII

A mixture of 2.5 parts of 5-methyl-3-(methylthio)-1-(4-nitrophenyl)-1H-1,2,4-triazole and 120 parts of methanol is hydrogenated at normal pressure and at room temperature with 2 parts of platinum-on-charcoal catalyst 10%. After the calculated amount of hydrogen is taken up, the catalyst is filtered off and the filtrate is evaporated. The residue is crystallized from a mixture of 4-methyl-2-pentanone and petroleumether. The product is filtered off and dried, yielding 1.5 parts (68%) 4-[5-methyl-3-(methylthio)-1H-1,2,4-triazol-1-yl]benzenamine; mp. 130°–136° C.

Following the same hydrogenation-procedure there is also prepared:
4-[3-(methylthio)-1H-1,2,4-triazol-1-yl]benzenamine as a residue.

Example IX

A mixture of 41 parts of 5-ethyl-3-(methylthio)-1-(4-nitrophenyl)-1H-1,2,4-triazole and 80 parts of methanol is hydrogenated at normal pressure and at room temperature with 1 part of palladium-on-charcoal catalyst 10%. After the calculated amount of hydrogen is taken up, the catalyst is filtered off and the filtrate is evaporated. The residue is crystallized from 1,1'-oxybisbutane. The product is filtered off and dried, yielding 33 parts (91%) of 4-[5-ethyl-3-(methylthio)-1H-1,2,4-triazol-1-yl]benzenamine; mp. 131.7° C.

In a similar manner there is also prepared:
4-(2-methyl-1H-imidazol-1-yl)benzenamine; mp. 105° C.

Example X

A mixture of 20 parts of 4-[5-methyl-3-(methylthio)-1H-1,2,4-triazol-1-yl]benzenamine, 15 parts of Raney-nickel catalyst and 400 parts of methanol is stirred and refluxed for 2 hours. The Raney-nickel is filtered off and another 15 parts of the catalyst are added. Stirring at reflux is continued for 4 hours. The reaction mixture is filtered, washed on the filter with methanol and the filtrate is evaporated. The residue is crystallized from a mixture of 4-methyl-2-pentanone, 2,2'-oxybispropane and petroleumether. The product is filtered off and dried, yielding 7.6 parts (47%) of 4-(5-methyl-1H-1,2,4-triazol-1-yl)benzenamine; mp. 145° C.

Example XI

A mixture of 35 parts of 1-(4-nitrophenyl)-5-propyl-1H-1,2,4-triazole-3-thiol, 83 parts of concentrated nitric acid solution and 150 parts of water is stirred and warmed to 60° C. While stirring, the mixture is allowed to cool to room temperature and the whole is further stirred overnight at room temperature. The precipitated product is filtered off, washed with water and added to a hot solution of 20 parts of potassium carbonate in 200 parts of water at 100° C. The reaction mixture is allowed to cool to room temperature while stirring. The precipitated product is filtered off, dried and crystallized from a mixture of 4-methyl-2-pentanone and 2,2'-oxybispropane. The product is filtered off and recrystallized from 4-methyl-2-pentanone, yielding 19.8 parts of 3,3'-dithiobis[1-(4-nitrophenyl)-5-propyl-1H-1,2,4-triazole]; mp. 171.5° C.

20 Parts of 3,3'-dithiobis[1-(4-nitrophenyl)-5-propyl-1H-1,2,4-triazole] are dissolved in 100 parts of acetic acid while stirring and warming. Then there are added dropwise 55 parts of hydrogen peroxide solution 30%: reflux temperature is reached. Upon completion, stirring at reflux is continued for 1 hour. The reaction mixture is cooled and poured onto a mixture of crushed ice and a sodium hydroxide solution 50%. The precipitated product is filtered off and dissolved in dichloromethane. The solution is washed with a sodium sulfite solution, dried, filtered and evaporated. The residue is purified by column-chromatography over silica gel using trichloromethane as eluent. The pure fractions are collected and the eluent is evaporated. The residue is converted into the hydrochloride salt in 2-propanol. The salt is filtered off and crystallized from ethanol, yielding 3.9 parts (19%) of 1-(4-nitrophenyl)-5-propyl-1H-1,2,4-triazole monohydrochloride; mp. 178.7° C.

A mixture of 38.3 parts of 1-(4-nitrophenyl)-5-propyl-1H-1,2,4-triazole monohydrochloride and 400 parts of methanol is hydrogenated at normal pressure and at room temperature with 3 parts of palladium-on-charcoal catalyst 10%. After the calculated amount of hydrogen is taken up, the catalyst is filtered off and the filtrate is evaporated. The residue is dissolved in water and neutralized with sodium hydrogen carbonate. The product is extracted with dichloromethane. The extract is washed with water, dried, filtered and evaporated. The residue is converted into the hydrochloride salt in 2-propanol. The salt is filtered off and dried, yielding 35 parts (91%) of 4-(5-propyl-1H-1,2,4-triazol-1-yl)benzenamine dihydrochloride.

Example XII

A mixture of 4 parts of N-(4-nitrophenyl)hydrazinecarboxamide, 5 parts of ethanimidamide hydrochloride and 5 parts of sodium acetate is stirred and heated for 4 hours at 140° C. The reaction mixture is cooled, water is added and the whole is stirred till the product is crystallized. It is filtered off and recrystallized from 2-propanol, yielding 1.5 parts (34%) of 2,4-dihydro-5-methyl-4-(4-nitrophenyl)-3H-1,2,4-triazol-3-one; mp. 226.1° C.

To a stirred solution of 13.5 parts of 2,4-dihydro-5-methyl-4-(4-nitrophenyl)-3H-1,2,4-triazol-3-one in 100 parts of dimethyl sulfoxide are added 2 parts of sodium hydride dispersion 78% and the whole is stirred till foaming has ceased. Then there are added dropwise 8.1 parts of dimethyl sulfate. Upon completion, stirring is continued for 3 hours at room temperature. The reaction mixture is poured onto water and the product is extracted three times with trichloromethane. The combined extracts are washed with water, dried, filtered and evaporated. The residue is crystallized from a mixture of 2-propanol and 2,2'-oxybispropane. The product is filtered off and recrystallized from 4-methyl-2-pentanone, yielding 6.3 parts of 2,4-dihydro-2,5-dimethyl-4-(4-nitrophenyl)-3H-1,2,4-triazol-3-one; mp. 153.2° C.

A mixture of 9 parts of 2,4-dihydro-2,5-dimethyl-4-(4-nitrophenyl)-3H-1,2,4-triazol-3-one and 200 parts of methanol is hydrogenated at normal pressure and at room temperature with 3 parts of Raney-nickel catalyst. After the calculated amount of hydrogen is taken up, the catalyst is filtered off and the filtrate is evaporated. The residue is triturated in 2,2'-oxybispropane. The product is filtered off and dried, yielding 7.5 parts (95%) of 4-(4-aminophenyl)-2,4-dihydro-2,5-dimethyl-3H-1,2,4-triazol-3-one; mp. 160° C.

Example XIII

A mixture of 53 parts of N-{4-[4-(4-methoxyphenyl)-1-piperazinyl]phenyl}hydrazinecarboxamide, 53 parts of ethanimidamide hydrochloride and 135 parts of N,N-dimethylformamide is stirred and heated for 3 hours at 130° C. The reaction mixture is cooled and poured onto water. The precipitated product is filtered off, washed with water and with methanol, and crystallized from N,N-dimethylformamide. The product is filtered off and recrystallized from 1,4-dioxane, yielding 19.5 parts of 2,4-dihydro-4-{4-[4-(4-methoxyphenyl)-1-piperazinyl]phenyl}-5-methyl-3H-1,2,4-triazol-3-one; 298.4° C.

Example XIV 19.2 Parts of 2,4-dihydro-4-{4-[4-(4-methoxyphenyl)-1-piperazinyl]phenyl}-3H-1,2,4-triazol-3-one are dissolved in 450 parts of dimethyl sulfoxide at about 100° C. Then there are added 3.1 parts of sodium hydride dispersion 50% and the whole is stirred till a temperature of about 50° C. is reached. 8.2 Parts of dimethyl sulfate are added and stirring is continued overnight at room temperature. The reaction mixture is poured onto water and the product is extracted with trichloromethane. The extract is dried, filtered and evaporated. The residue is purified by column-chromatography over silica gel using a mixture of trichloromethane and methanol (98:2 by volume) as eluent. The pure fractions are collected and the eluent is evaporated. The residue is crystallized from 1-butanol, yielding 5.8 parts of 2,4-dihydro-4-{4-[4-(4-methoxyphenyl)-1-piperazinyl]phenyl}-2-methyl-3H-1,2,4-triazol-3-one; mp. 245.7° C.

Example XV

10 Parts of 2,4-dihydro-4-{4-[4-(4-methoxyphenyl)-1-piperazinyl]phenyl}-3H-1,2,4-triazol-3-one are dissolved in 300 parts of dimethyl sulfoxide at 100° C. Then there are added 1.6 parts of sodium hydride dispersion 50% and stirring is continued while the mixture is allowed to cool to about 50° C. 3.9 Parts of 1-bromopropane are added and the whole is stirred overnight at room temperature. The reaction mixture is poured onto water and the product is extracted with trichloromethane. The extract is washed with water, dried, filtered and evaporated. The residue is purified by column-chromatography over silica gel using a mixture of trichloromethane and methanol (98:2 by volume) as eluent. The pure fractions are collected and the eluent is evaporated. The residue is triturated in 2-propanol. The product is filtered off and dried; yielding 7.5 parts (65%) of 2,4-dihydro-4-{4-[4-(4-methoxyphenyl)-1-piperazinyl]phenyl}-2-propyl-3H-1,2,4-triazol-3-one.

Following the same N-alkylation-procedure and using equivalent amounts of the appropriate starting materials there are prepared:

2-ethyl-2,4-dihydro-4-{4-[4-(4-methoxyphenyl)-1-piperazinyl]phenyl}-5-methyl-3H-1,2,4-triazol-3-one; mp. 179.8° C.

2,4-dihydro-4-{4-[4-(4-methoxyphenyl)-1-piperazinyl]phenyl}-5-methyl-2-propyl-3H-1,2,4-triazol-3-one; mp. 144.5° C.; and 2-ethyl-2,4-dihydro-4-{4-[4-(4-methoxyphenyl)-1-piperazinyl]phenyl}-3H-1,2,4-triazol-3-one; mp. 210.2° C.

Example XVI

A mixture of 12.5 parts of N,N-bis(2-chloroethyl)-4-methoxybenzenamine, 8 parts of 4-(1H-pyrazol-1-yl)benzenamine, 2 parts of potassium iodide, 80 parts of 2-propanone and 100 parts of water is stirred and refluxed for 24 hours. The reaction mixture is cooled. The precipitated product is filtered off (the filtrate is set aside), washed with water and with 2-propanone, yielding a first crude fraction of 6 parts. The filtrate (see above) is neutralized with a sodium hydrogen carbonate solution and extracted with trichloromethane. The extract is dried, filtered and evaporated. The residue is triturated in 2-propanol. The product is filtered off and washed with methanol, yielding a second crude fraction of 2 parts. The combined crude crops (resp. 6 and 2 parts) are crystallized from 1-butanol, yielding 7.1 parts of 1-(4-methoxyphenyl)-4-[4-(1H-pyrazol-1-yl)phenyl]-piperazine; mp. 207.7° C.

Following the same procedure and using equivalent amounts of the appropriate starting materials there are also prepared:

1-[4-(1H-imidazol-1-yl)phenyl]-4-(4-methoxyphenyl)-piperazine; mp. 255°–256° C.;
1-(4-methoxyphenyl)-4-[4-(1H-1,2,4-triazol-1-yl)phenyl]piperazine; mp. 230.3° C.;
1-(4-methoxyphenyl)-4-{4-[3-(methylthio)-1H-1,2,4-triazol-1-yl]phenyl}piperazine; mp. 186.5° C.;
1-(4-methoxyphenyl)-4-{4-[5-methyl-3-(methylthio)-1H-1,2,4-triazol-1-yl]phenyl}piperazine; mp. 153.3° C.;
1-(4-methoxyphenyl)-4-[4-(5-methyl-1H-1,2,4-triazol-1-yl)phenyl]piperazine; mp. 191.1° C.;
2,4-dihydro-4-{4-[4-(4-methoxyphenyl)-1-piperazinyl]phenyl}-2,5-dimethyl-3H-1,2,4-triazol-3-one; mp. 196.7° C.;
1-(4-methoxyphenyl)-4-[4-(5-propyl-1H-1,2,4-triazol-1-yl)phenyl]piperazine; mp. 196.3° C.;
1-{4-[5-ethyl-3-(methylthio)-1H-1,2,4-triazol-1-yl]phenyl}-4-(4-methoxyphenyl)piperazine; mp. 142.3° C.; and
1-(4-methoxyphenyl)-4-[4-(2-methyl-1H-imidazol-1-yl)phenyl]piperazine; mp. 178.5° C.

Example XVII

A mixture of 6 parts of 4-[4-(4-methoxyphenyl)-1-piperazinyl]benzenamine, 3.6 parts of phenyl carbonochloridate, 75 parts of pyridine and 98 parts of dichloromethane is stirred and warmed till all solid enters solution. Stirring is continued for 30 minutes at room temperature. The reaction mixture is poured onto 500 parts of water and 210 parts of 2,2'-oxybispropane are added. The whole is stirred for a while. The precipitated product is filtered off and crystallized from 1-butanol, yielding 5.2 parts (61%) of phenyl{4-[4-(4-methoxyphenyl)-1-piperazinyl]phenyl}carbamate; mp. 204.5° C.

A mixture of 3.2 parts of phenyl{4-[4-(4-methoxyphenyl)-1-piperazinyl]phenyl}carbamate, 50 parts of hydrazine hydrate and 100 parts of 1,4-dioxane is stirred and refluxed for 3 hours. The reaction mixture is cooled and poured onto water. The precipitated product is filtered off and crystallized from N,N-dimethylformamide, yielding 1.7 parts (63%) of N-{4-[4-(4-methoxyphenyl)-1-piperazinyl]-phenyl}hydrazinecarboxamide; mp. +300° C.

A mixture of 3.4 parts of N-{4-[4-(4-methoxyphenyl)-1-piperazinyl]phenyl}hydrazinecarboxamide, 3 parts of methanimidamide acetate and 10 parts of dimethyl sulfoxide is stirred and heated for 2 hours at 100° C. The reaction mixture is cooled and poured onto a mixture of 4-methyl-2-pentanone and 2,2'-oxybispropane. The precipitated product is filtered off and crystallized from N,N-dimethylformamide (activated charcoal), yielding 1 part (28%) of 2,4-dihydro-4-{4-[4-(4-methoxyphenyl)-1-piperazinyl]phenyl}-3H-1,2,4-triazol-3-one; mp. +300° C.

Example XVIII

A mixture of 30 parts of 4-[4-(4-methoxyphenyl)-1-piperazinyl]benzenamine and 300 parts of a hydrobromic acid solution 48% in water is stirred and refluxed for 10 days. The reaction mixture is evaporated and the residue is alkalized with sodium hydroxide. The mixture is filtered and the filtrate is acidified with acetic acid. The precipitated product is filtered off and crystallized from 1,4-dioxane, yielding 12 parts (44%) of 4-[4-(4-aminophenyl)-1-piperazinyl]phenol.

Following the same procedure and using equivalent amounts of the appropriate starting materials there are also prepared:

4-{4-[4-(1H-pyrazol-1-yl)phenyl]-1-piperazinyl}phenol;
4-{4-[4-(1H-imidazol-1-yl)phenyl]-1-piperazinyl}-phenol; mp. >260° C.
4-{4-[4-(1H-1,2,4-triazol-1-yl)phenyl]-1-piperazinyl}-phenol; mp. 276.6° C.
4-[4-{4-[3-(methylthio)-1H-1,2,4-triazol-1-yl]phenyl}-1-piperazinyl]phenol; mp. 225.5° C.
4-[4-{4-[5-methyl-3-(methylthio)-1H-1,2,4-triazol-1-yl]phenyl}-1-piperazinyl]phenol; mp. 255.8° C.
4-[4-{4-[3-methyl-5-(methylthio)-4H-1,2,4-triazol-4-yl]phenyl}-1-piperazinyl]phenol;
4-{4-[4-(5-methyl-1H-1,2,4-triazol-1-yl)phenyl]-1-piperazinyl}phenol; mp. 281.1° C.
4-[4-{4-[3-(methylthio)-4H-1,2,4-triazol-4-yl]phenyl}-1-piperazinyl]phenol;
2,4-dihydro-4-{4-[4-(4-hydroxyphenyl)-1-piperazinyl]phenyl}-2,5-dimethyl-3H-1,2,4-triazol-3-one; mp. +260° C.;
2,4-dihydro-4-{4-[4-(4-hydroxyphenyl)-1-piperazinyl]phenyl}-2-propyl-3H-1,2,4-triazol-3-one;
4-{4-[4-(2-methyl-1H-imidazol-1-yl)phenyl]-1-piperazinyl}-phenol; mp. +300° C.;
4-[4-{4-[5-ethyl-3-(methylthio)-1H-1,2,4-triazol-1-yl]phenyl}-1-piperazinyl]phenol; mp. 232.6° C.;
2-ethyl-2,4-dihydro-4-{4-[4-(4-hydroxyphenyl)-1-piperazinyl]phenyl}-5-methyl-3H-1,2,4-triazol-3-one; mp. 287.8° C.;
2,4-dihydro-4-{4-[4-(4-hydroxyphenyl)-1-piperazinyl]phenyl}-5-methyl-2-propyl-3H-1,2,4-triazol-3-one; mp. 258.2° C.;
2,4-dihydro-4-{4-[4-(4-hydroxyphenyl)-1-piperazinyl]phenyl}-2-methyl-3H-1,2,4-triazol-3-one;
2-ethyl-2,4-dihydro-4-{4-[4-(4-hydroxyphenyl)-1-piperazinyl]phenyl}-3H-1,2,4-triazol-3-one; mp. 217° C.; and
4-{4-[4-(5-propyl-1H-1,2,4-triazol-1-yl)phenyl]-1-piperazinyl}phenol; mp. 225.6° C.

B. PREPARATION OF FINAL COMPOUNDS

Example XIX

To a stirred solution of 3 parts of 4-[4-(4-aminophenyl)-1-piperazinyl]phenol in 50 parts of dimethylsulfoxide are added 0.5 parts of a sodium hydride dispersion 50%. The whole is stirred at 50° C. till foaming has ceased. Then there are added 4.1 parts of cis-[2-(2,4-dichlorophenyl)-2-(1H-imidazol-2-ylmethyl)-1,3-dioxolan-4-ylmethyl]methanesulfonate and stirring is continued for 2 hours at 70° C. The reaction mixture is cooled and poured onto water. The product is extracted with dichloromethane. The extract is washed with a diluted sodium hydroxide solution, dried, filtered and evaporated. The residue is purified by column-chromatography over silica gel using a mixture of trichloromethane and methanol (98:2 by volume) as eluent. The pure fractions are collected and the eluent is evaporated. The residue is crystallized from 2-propanol. The product is filtered off and dried, yielding 1.3 parts (22%) of cis-4-[4-{4-[2-(2,4-dichlorophenyl)-2-(1H-imidazol-1-ylmethyl)-1,3-dioxolan-4-ylmethoxy]-phenyl}-1-piperazinyl]benzenamine; mp. 174.4° C.

Example XX

To a solution of 3.2 parts of 4-{4-[4-(1H-pyrazol-1-yl)phenyl]-1-piperazinyl}phenol in 100 parts of dimethyl sulfoxide are added 0.32 parts of a sodium hydride dispersion 78% and the whole is stirred at 50° C. till foaming has ceased. Then 4.1 parts of cis-2-(2,4-dichlorophenyl)-2-(1H-imidazol-1-ylmethyl)-1,3-dioxolan-4-ylmethyl methanesulfonate are added and stirring is continued for 3 hours at 100° C. The reaction mixture is cooled, poured onto water and the product is extracted with dichloromethane. The extract is washed with diluted sodium hydroxide solution, dried, filtered and evaporated. The residue is purified by column-chromatography over silica gel using a mixture of trichloromethane and methanol (98:2 by volume) as eluent. The pure fractions are collected and the eluent is evaporated.

The residue is purified again by column-chromatography over silica gel using a mixture of methylbenzene and ethanol (95:5 by volume) as eluent. The pure fractions are collected and the eluent is evaporated. The residue is crystallized from methylbenzene, yielding 2.2 parts (34%) of cis-1-{4-[2-(2,4-dichlorophenyl)-2-(1H-imidazol-1-ylmethyl)-1,3-dioxolan-4-ylmethoxy]-phenyl}-4-[4-(1H-pyrazol-1-yl)phenyl]piperazine; mp. 195.1° C.

Following the same procedure and using equivalent amounts of the appropriate starting materials there are also prepared:

cis-1-{4-[2-(2,4-dichlorophenyl)-2-(1H-imidazol-1-ylmethyl)-1,3-dioxolan-4-ylmethoxy]-phenyl-4-[4-(1H-imidazol-1-yl)phenyl]piperazine; mp. 166.7° C.

cis-1-{4-[2-(2,4-dichlorophenyl)-2-(1H-imidazol-1-ylmethyl)-1,3-dioxolan-4-ylmethoxy]-phenyl}-4-[4-(1H-1,2,4-triazol-1-yl)phenyl]piperazine; mp. 175.3° C.

cis-1-{4-[2-(2,4-dichlorophenyl)-2-(1H-imidazol-1-ylmethyl)-1,3-dioxolan-4-ylmethoxy]-phenyl}-4-{4-[3-(methylthio)-1H-1,2,4-triazol-1-yl]phenyl}piperazine; mp. 178.3° C.

cis-1-{4-[2-(2,4-dichlorophenyl)-2-(1H-imidazol-1-ylmethyl)-1,3-dioxolan-4-ylmethoxy]phenyl}-4-{4-[3-methyl-5-(methylthio)-4H-1,2,4-triazol-4-yl]phenyl}piperazine; mp. 127.8° C.

cis-1-{4-[2-(2,4-dichlorophenyl)-2-(1H-imidazol-1-ylmethyl)-1,3-dioxolan-4-ylmethoxy]-phenyl}-4-[4-(5-methyl-3-(methylthio)-1H-1,2,4-triazol-1-yl)phenyl]piperazine; mp. 188.9° C.

cis-1-{4-[2-(2,4-dichlorophenyl)-2-(1H-imidazol-1-ylmethyl)-1,3-dioxolan-4-ylmethoxy]phenyl}-4-{4-[3-(methylthio)-4H-1,2,4-triazol-4-yl]phenyl}piperazine; mp. 176.4;

cis-4-{4-[4-{4-[2-(2,4-dichlorophenyl)-2-(1H-imidazol-1-ylmethyl)-1,3-dioxolan-4-ylmethoxy]phenyl}-1-piperazinyl]phenyl}-2,4-dihydro-2,5-dimethyl-3H-1,2,4-triazol-3-one; mp. 149.3° C.;

cis-4-{4-[4-{4-[2-(2,4-dichlorophenyl)-2-(1H-imidazol-1-yl-methyl)-1,3-dioxolan-4-ylmethoxy]phenyl}-1-piperazinyl]phenyl}-2,4-dihydro-2-propyl-3H-1,2,4-triazol-3-one; mp. 185.7° C.;

cis-1-{4-[2-(2,4-dichlorophenyl)-2-(1H-imidazol-1-ylmethyl)-1,3-dioxolan-4-ylmethoxy]-phenyl}-4-[4-(5-methyl-1H-1,2,4-triazol-1-yl)phenyl]piperazine; mp. 154.1° C.;

cis-1-{4-[2-(2,4-dichlorophenyl)-2-(1H-imidazol-1-ylmethyl)-1,3-dioxolan-4-ylmethoxy]phenyl}-4-[4-(2-methyl-1H-imidazol-1-yl)phenyl]piperazine; mp. 180.1° C.;

cis-4-{4-[4-{4-[2-(2,4-dichlorophenyl)-2-(1H-imidazol-1-ylmethyl)-1,3-dioxolan-4-ylmethoxy]phenyl}-1-piperazinyl]phenyl}-2,4-dihydro-3H-1,2,4-triazol-3-one; mp. 212.8° C.;

cis-4-{4-[4-{4-[2-(2,4-dichlorophenyl)-2-(1H-imidazol-1-ylmethyl)-1,3-dioxolan-4-ylmethoxy]phenyl}-1-piperazinyl]phenyl}-2-ethyl-2,4-dihydro-3H-1,2,4-triazol-3-one; mp. 204.7° C.;

cis-4-{4-[4-{4-[2-(2,4-dichlorophenyl)-2-(1H-imidazol-1-ylmethyl)-1,3-dioxolan-4-ylmethoxy]phenyl}-1-piperazinyl]phenyl}-2,4-dihydro-5-methyl-2-propyl-3H-1,2,4-triazol-3-one monohydrate; mp. 153.9° C.;

cis-1-{4-[2-(2,4-dichlorophenyl)-2-(1H-imidazol-1-ylmethyl)-1,3-dioxolan-4-ylmethoxy]phenyl}-4-{4-[5-ethyl-3-(methylthio)-1H-1,2,4-triazol-1-yl]phenyl}-piperazine; mp. 136.3° C.;

cis-1-{4-[2-(2,4-dichlorophenyl)-2-(1H-imidazol-1-ylmethyl)-1,3-dioxolan-4-ylmethoxy]phenyl}-4-[4-(5-propyl-1H-1,2,4-triazol-1-yl)phenyl]piperazine; mp. 150.4° C.; and cis-4-{4-[4-{4-[2-(2,4-dichlorophenyl)-2-(1H-imidazol-1-ylmethyl)-1,3-dioxolan-4-ylmethoxy]phenyl}-1-piperazinyl]phenyl}-2-ethyl-2,4-dihydro-5-methyl-3H-1,2,4-triazol-3-one monohydrate; mp. 135.5° C.

Example XXI

A mixture of 2 parts of sodium azide, 5.8 parts of cis-4-[4-{4-[2-(2,4-dichlorophenyl)-2-(1H-imidazol-1-yl)-1,3-dioxolan-4-ylmethoxy]phenyl}-1-piperazinyl]-benzenamine, 4 parts of 1,1',1''-[methylidynetris(oxy)]-trisethane and 50 parts of acetic acid is stirred and heated overnight at 70° C. The reaction mixture is cooled and neutralized with a potassium carbonate solution. The product is extracted with dichloromethane. The extract is dried, filtered and evaporated. The residue is purified by column-chromatography over silica gel using a mixture of trichloromethane and methanol (98:2 by volume) as eluent. The pure fractions are collected and the eluent is evaporated. The residue is crystallized from 1-butanol. The product is filtered off and dried, yielding 3.8 parts (60%) of cis-1-{4-[2-(2,4-dichlorophenyl)-2-(1H-imidazol-1-yl-methyl)-1,3-dioxolan-4-ylmethoxy]phenyl}-4-[4-(1H-tetrazol-1-yl)phenyl]piperazine; mp. 201.3° C.

Example XXII

To a stirred solution of 8 parts of 4-[4-(4-aminophenyl)-1-piperazinyl]phenol in 100 parts of dimethyl sulfoxide are added 1.5 parts of sodium hydride dispersion 50% and stirring is continued till foaming has ceased. Then there are added 12.3 parts of cis-[2-(2,4-dichlorophenyl)-2-(1H-1,2,4-triazol-1-ylmethyl)-1,3-dioxolan-4-ylmethyl]methanesulfonate and the whole is stirred and heated for 4 hours at 50° C. The reaction mixture is cooled and poured onto water. The product is extracted three times with dichloromethane. The combined extracts are washed with a diluted sodium hydroxide solution and treated with activated charcoal. The latter is filtered off and the filtrate is evaporated. The residue is purified by column-chromatography over silica gel using a mixture of trichloromethane and methanol (98:2 by volume) as eluent. The pure fractions are collected and the eluent is evaporated. The residue is crystallized from 1-butanol, yielding 5.1 parts of cis-4-[4-{4-[2-(2,4-dichlorophenyl)-2-(1H-1,2,4-triazol-1- ylmethyl)-1,3-dioxolan-4-ylmethoxy]phenyl}-1-piperazinyl]benzenamine; mp. 186.8° C.

Example XXIII

To a stirred solution of 3 parts of 4-{4-[4-(1H-1,2,4-triazol-1-yl)phenyl]-1-piperazinyl}phenol in 100 parts of dimethyl sulfoxide are added 0.3 parts of sodium hydride dispersion 78% and the whole is stirred at 50° C. till foaming has ceased. Then there are added 3.7 parts of cis-[2-(2,4-dichlorophenyl)-2-(1H-1,2,4-triazol-1-ylmethyl)-1,3-dioxolan-4-ylmethyl]methanesulfonate and stirring is continued for 3 hours at 100° C. The reaction mixture is cooled and poured onto water. The product is extracted three times with dichloromethane. The combined extracts are washed with a diluted sodium hydroxide solution, dried, filtered and evaporated. The residue is crystallized from 1-butanol. The product is filtered off and dried, yielding 4.3 parts (75%) of cis-1-{4-[2-(2,4-dichlorophenyl)-2-(1H-1,2,4-triazol-1-ylmethyl)-1,3-dioxolan-4-ylmethoxy]phenyl}-4-[4-(1H-1,2,4-triazol-1-yl)phenyl]piperazine; mp. 219.6° C.

Following the same procedure and using equivalent amounts of the appropriate starting materials there are also prepared:

cis-1-{4-[2-(2,4-dichlorophenyl)-2-(1H-1,2,4-triazol-1-ylmethyl)-1,3-dioxolan-4-ylmethoxy]phenyl}-4-[4-(1H-pyrazol-1-yl)phenyl]piperazine; mp. 188.3° C.

cis-1-{4-[2-(2,4-dichlorophenyl)-2-(1H-1,2,4-triazol-1-ylmethyl)-1,3-dioxolan-4-ylmethoxy]phenyl}-4-[4-(1H-imidazol-1-yl)phenyl]piperazine; mp. 194.3° C.

cis-1-{4-[2-(2,4-dichlorophenyl)-2-(1H-1,2,4-triazol-1-ylmethyl)-1,3-dioxolan-4-ylmethoxy]-phenyl}-4-[4-(5-methyl-1H-1,2,4-triazol-1-yl)phenyl]piperazine; mp. 166.5° C.

cis-1-{4-[2-(2,4-dichlorophenyl)-2-(1H-1,2,4-triazol-1-ylmethyl)-1,3-dioxolan-4-ylmethoxy]phenyl}-4-{4-[3-(methylthio)-1H-1,2,4-triazol-1-yl]phenyl}piperazine; mp. 153.9° C.

cis-1-{4-[2-(2,4-dichlorophenyl)-2-(1H-1,2,4-triazol-1-ylmethyl)-1,3-dioxolan-4-ylmethoxy]-phenyl}-4-{4-[5-methyl-3-(methylthio)-1H-1,2,3-triazol-1-yl]phenyl}piperazine; mp. 164.1° C.

cis-4-{4-[4-{4-[2-(2,4-dichlorophenyl)-2-(1H-1,2,4-triazol-1-ylmethyl)-1,3-dioxolan-4-yl-methoxy]-phenyl}-1-piperazinyl]phenyl}-3-(methylthio)-4H-1,2,4-triazole; mp. 147°–152.6° C.

cis-1-{4-[2-(2,4-dichlorophenyl)-2-(1H-1,2,4-triazol-1-ylmethyl)-1,3-dioxolan-4-ylmethoxy]phenyl}-4-{4-[3-methyl-5-(methylthio)-4H-1,2,4-triazol-4-yl]phenyl}-piperazine; mp. 118.3° C.

cis-4-{4-[4-{4-[2-(2,4-dichlorophenyl)-2-(1H-1,2,4-triazol-1-ylmethyl)-1,3-dioxolan-4-ylmethoxy]-phenyl}-1-piperazinyl]phenyl}-2,4-dihydro-2,5-dimethyl-3H-1,2,4-triazol-3-one monohydrate; mp. 161.9° C.;

cis-4-{4-[4-{4-[2-(2,4-dichlorophenyl)-2-(1H-1,2,4-triazol-1-ylmethyl)-1,3-dioxolan-4ylmethoxy]-phenyl}-1-piperazinyl]phenyl}-2,4-dihydro-2-propyl-3H-1,2,4-triazol-3-one; mp. 167.3° C.;

cis-1-{4-[2-(2,4-dichlorophenyl)-2-(1H-1,2,4-triazol-1-yl-methyl)-1,3-dioxolan-4-ylmethoxy]phenyl}-4-[4-(2-methyl-1H-imidazol-1-yl)phenyl]piperazine; mp. 175.6° C.;

cis-4-{4-[4-{4-[2-(2,4-dichlorophenyl)-2-(1H-1,2,4-triazol-1-ylmethyl)-1,3-dioxolan-4-ylmethoxy]-phenyl}-1-piperazinyl]phenyl}-2,4-dihydro-2-methyl-3H-1,2,4-triazol-3-one; mp. 193.8° C.;

cis-4-{4-[4-{4-[2-(2,4-dichlorophenyl)-2-(1H-1,2,4-triazol-1-ylmethyl)-1,3-dioxolan-4-ylmethoxy]phenyl}-1-piperazinyl]phenyl}-2-ethyl-2,4-dihydro-5-methyl-3H-1,2,4-triazol-3-one; mp. 178.3° C.;

cis-4-{4-[4-{4-[2-(2,4-dichlorophenyl)-2-(1H-1,2,4-triazol-1-ylmethyl)-1,3-dioxolan-4-ylmethoxy]-phenyl}-1-piperazinyl]phenyl}-2,4-dihydro-5-methyl-2-propyl-3H-1,2,4-triazol-3-one monohydrate; mp. 165.5° C.;

cis-4-{4-[4-{4-[2-(2,4-dichlorophenyl)-2-(1H-1,2,4-triazol-1-ylmethyl)-1,3-dioxolan-4-ylmethoxy]-phenyl}-1-piperazinyl]phenyl}-2-ethyl-2,4-dihydro-3H-1,2,4-triazol-3-one; mp. 186° C.; and cis-1-{4-[2-(2,4-dichlorophenyl)-2-(1H-1,2,4-triazol-1-yl-methyl)-1,3-dioxolan-4-ylmethoxy]phenyl}-4-[4-(5-propyl-1H-1,2,4-triazol-1-yl)phenyl]piperazine; mp. 140.9° C.

Example XXIV

A mixture of 4 parts of cis-4-[4-{4-[2-(2,4-dichlorophenyl)-2-(1H-1,2,4-triazol-1-ylmethyl)-1,3-dioxolan-4-yl-methoxy]phenyl}-1-piperazinyl]benzenamine, 0.5 parts of sodium azide, 1.08 parts of 1,1',1''-[methylidynetris(oxy)]trisethane and 50 parts of acetic acid is stirred for 5 hours at 70° C. Another 0.5 parts of sodium azide and 1.08 parts of 1,1',1''-[methylidynetris(oxy)]trisethane are added and stirring at 70° C. is continued for 15 hours. The reaction mixture is cooled and poured onto a mixture of potassium carbonate and water. The product is extracted with dichloromethane. The extract is dried, filtered and evaporated. The residue is purified by column-chromatography over silica gel using a mixture of trichloromethane and methanol (98:2 by volume) as eluent. The pure fractions are collected and the eluent is evaporated. The residue is crystallized from 1-butanol, yielding 2.1 parts (48%) of cis-1-{4-[2-(2,4-dichlorophenyl)-2-(1H-1,2,4-triazol-1-yl-methyl)-1,3-dioxolan-4-ylmethoxy]phenyl}-4-[4-(1H-tetrazol-1-yl)phenyl]piperazine; mp. 192.5° C.

Example XXV

To a stirred mixture of 5.7 parts of cis-4-[4-{4-[2-(2,4-dichlorophenyl)-2-(1H-imidazol-1-ylmethyl)-1,3-dioxolan-4-yl-methoxy]phenyl}-1-piperazinyl]benzenamine and 100 parts of acetic acid are added 1.5 parts of tetrahydro-2,5-dimethoxyfuran at 50° C. The whole is stirred and refluxed for 5 minutes. The reaction mixture is poured onto crushed ice and the whole is neutralized with a sodium hydroxide solution 50%. The product is extracted with dichloromethane. The extract is treated with activated charcoal. The latter is filtered off and the filtrate is evaporated. The residue is crystallized from 1-butanol, yielding 3.3 parts (52%) of cis-1-{4-[2-(2,4-dichlorophenyl)-2-(1H-imidazol-1-ylmethyl)-1,3-dioxolan-4-ylmethoxy]phenyl}-4-[4-(1H-pyrrol-1-yl)phenyl]piperazine; mp. 188.9° C.

In a similar manner there is also prepared:

cis-1-{4-[2-(2,4-dichlorophenyl)-2-(1H-1,2,4-triazol-1-yl-methyl)-1,3-dioxolan-4-ylmethoxy]phenyl}-4-[4-(1H-pyrrol-1-yl)phenyl]piperazine; mp. 184.9° C.

Example XXVI

A mixture of 40 parts of ethanimidamide hydrochloride, 20 parts of cis-N-{4-[4-{4-[2-(2,4-dichlorophenyl)-2-(1H-imidazol-1-ylmethyl)-1,3-dioxolan-4-ylmethoxy]-phenyl}-1-piperazinyl]phenyl}hydrazinecarboxamide, 40 parts of sodium acetate and 90 parts of N,N-dimethylformamide is stirred and heated for 4 hours at 130°

C. The reaction mixture is cooled and 100 parts of water are added. The precipitated product is filtered off, washed with water and with 2-propanol, and crystallized from 1-butanol, yielding 9 parts (44%) of cis-4-{4-[4-{4-[2-(2,4-dichlorophenyl)-2-(1H-imidazol-1-ylmethyl)-1,3-dioxolan-4-ylmethoxy]phenyl}-1-piperazinyl]phenyl}-2,4-dihydro-5-methyl-3H-1,2,4-triazol-3-one 2-propanolate (2:1); mp. 295.7° C.

In a similar manner there are also prepared:

cis-4-{4-[4-{4-[2-(2,4-dichlorophenyl)-2-(1H-imidazol-1-yl-methyl)-1,3-dioxolan-4-ylmethoxy]phenyl}-1-piperazinyl]phenyl}-5-ethyl-2,4-dihydro-3H-1,2,4-triazol-3-one; mp. 275.6° C.; and cis-4-{4-[4-{4-[2-(2,4-dichlorophenyl)-2-(1H-imidazol-1-yl-methyl)-1,3-dioxolan-4-ylmethoxy]phenyl}-1-piperazinyl]phenyl}-2,4-dihydro-3H-1,2,4-triazol-3-one; mp. 255° C.

Example XXVII

A mixture of 1.31 parts of 2-bromopropane, 5 parts of cis-4-{4-[4-{4-[2-(2,4-dichlorophenyl)-2-(1H-imidazol-1-yl-methyl)-1,3-dioxolan-4-ylmethoxy]phenyl}-1-piperazinyl]phenyl}-2,4-dihydro-3H-1,2,4-triazol-3-one and 100 parts of dimethyl sulfoxide is stirred at 50° C. and 0.4 parts of sodium hydride dispersion 50% are added. After stirring for 1 hour at 50° C., another 1.31 parts of 2-bromopropane and 0.4 parts of sodium hydride dispersion 50% are added and stirring is continued for 1 hour at 50° C. The reaction mixture is cooled and poured onto water. The product is extracted with dichloromethane. The extract is washed with water, dried, filtered and evaporated. The residue is purified by column-chromatography over silica gel using a mixture of trichloromethane and methanol (99:1 by volume) as eluent. The pure fractions are collected and the eluent is evaporated. The residue is crystallized from 4-methyl-2-pentanone, yielding 2 parts (37%) of cis-4-{4-[4-{4-[2-(2,4-dichlorophenyl)-2-(1H-imidazol-1-ylmethyl)-1,3-dioxolan-4-yl-methoxy]phenyl}-1-piperazinyl]phenyl}-2,4-dihydro-2-(1-methylethyl)-3H-1,2,4-triazol-3-one; mp. 222.1° C.

In a similar manner there are also prepared:

cis-2-butyl-4-{4-[4-{4-[2-(2,4-dichlorophenyl)-2-(1H-imidazol-1-ylmethyl)-1,3-dioxolan-4-ylmethoxy]-phenyl}-1-piperazinyl]phenyl}-2,4-dihydro-3H-1,2,4-triazol-3-one; mp. 199.2° C.; and cis-4-{4-[4-{4-[2-(2,4-dichlorophenyl)-2-(1H-imidazol-1-yl-methyl)-1,3-dioxolan-4-ylmethoxy]phenyl}-1-piperazinyl]phenyl}-5-ethyl-2,4-dihydro-2-propyl-3H-1,2,4-triazol-3-one; mp. 170.4° C.

Example XXVIII

Following the procedure described in Example XIX there are also prepared:

trans-3-[4-{4-[2-(5-bromo-2-thienyl)-2-(1H-imidazol-1-ylmethyl)-1,3-dioxolan-4-ylmethoxy]-phenyl}-1-piperazinyl]benzenamine;

4-[4-{4-[2-(2-chloro-6-methylphenyl)-2-(1H-1,2,4-triazol-1-yl-methyl)-1,3-dioxolan-4-ylmethoxy]-phenyl}-1-piperazinyl]benzenamine;

4-[4-{4-[2-(1H-imidazol-1-ylmethyl)-2-(4-methoxy-phenyl)-1,3-dioxolan-4-ylmethoxy]-phenyl}-1-piperazinyl]benzenamine;

3-[4-{4-[2-(5-chloro-2-thienyl)-2-(1H-1,2,4-triazol-1-ylmethyl)-1,3-dioxolan-4-ylmethoxy]-phenyl}-1-piperazinyl]benzenamine.

Example XXIX

Following the procedure described in Example XX there are also prepared:

cis-1-{4-[2-(3-ethoxyphenyl)-2-(1H-imidazol-1-ylmethyl)-1,3-dioxolan-4-ylmethoxy]-phenyl}-4-[4-(3-methyl-1H-pyrrol-1-yl)phenyl]piperazine;

1-{3-[2-(1H-imidazol-1-ylmethyl)-2-(2-thienyl)-1,3-dioxolan-4-ylmethoxy]-phenyl}-4-[3-(4-phenyl-1H-pyrrol-1-yl)phenyl]piperazine;

trans-1-{4-[2-(4-bromophenyl)-2-(1H-1,2,4-triazol-1-ylmethyl)-1,3-dioxolan-4-ylmethoxy]-phenyl}-4-[4-(1H-pyrrol-1-yl)phenyl]piperazine;

cis-1-{3-[2-(4-bromo-2-thienyl)-2-(1H-1,2,4-triazol-1-ylmethyl)-1,3-dioxolan-4-ylmethoxy]-phenyl}-4-[4-(2,5-diethyl-1H-pyrrol-1-yl)phenyl]piperazine;

4-[3-(4-methyl-1H-pyrazol-1-yl)phenyl]-1-{4-[2-(2-thienyl)-2-(1H-1,2,4-triazol-1-ylmethyl)-1,3-dioxolan-4-ylmethoxy]phenyl}piperazine;

trans-1-{4-[2-(5-bromo-2-thienyl)-2-(1H-imidazol-1-ylmethyl)-1,3-dioxolan-4-ylmethoxy]phenyl}-4-[4-(2-ethylthio-4-phenyl-1H-imidazol-1-yl)phenyl]piperazine;

cis-4-[4-(5-ethyl-2-mercapto-1H-imidazol-1-yl)phenyl]-1-{3-[2-phenyl-2-(1H-1,2,4-triazol-1ylmethyl)-1,3-dioxolan-4-ylmethoxy]phenyl}piperazine;

1-{4-[2-(4-bromo-2-ethoxyphenyl)-2-(1H-imidazol-1-ylmethyl)-1,3-dioxolan-4-ylmethoxy]phenyl}-4-[3-(5-phenyl-1H-1,2,4-triazol-1-yl)phenyl]piperazine;

trans 1-{3-[2-(5-chloro-2-thienyl)-2-(1H-1,2,4-triazol-1-ylmethyl)-1,3-dioxolan-4-ylmethoxy]phenyl}-4-[2-(3-methylthio-5-pentyl-4H-1,2,4-triazol-4-yl)phenyl]piperazine;

4-{4-[4-{4-[2-(2,6-diethoxyphenyl)-2-(1H-imidazol-1-ylmethyl)-1,3-dioxolan-4-ylmethoxy]phenyl}-1-piperazinyl]phenyl}-2,4-dihydro-2-phenylmethyl-3H-1,2,4-triazol-3-one;

cis 4-{4-[4-{4-[2-(2-thienyl)-2-(1H-1,2,4-triazol-1-ylm ethyl)-1,3-dioxolan-4-ylmethoxy]phenyl}-1-piperazinyl]phenyl}-2,4-dihydro-2-methyl-5-phenyl-methyl-3H-1,2,4-triazol-3-one;

Example XXX

Following the procedure described in Example XXI there are also prepared:

1-{4-[2-(4-fluorophenyl)-2-(1H-imidazol-1-ylmethyl)-1,3-dioxolan-4-ylmethoxy]phenyl}-4-[4-(5-methylthio-1H-tetrazol-1-yl)-phenyl]piperazine;

trans 1-{4-[2-(5-chloro-2-thienyl)-2-(1H-1,2,4-triazol-1-ylmethyl)-1,3-dioxolan-4-ylmethoxy]phenyl}-4-[4-(5-phenylethyl-1H-tetrazol-1-yl)phenyl]piperazine.

What is claimed is:

1. A chemical compound selected from the group consisting of an azole derivative having the formula:

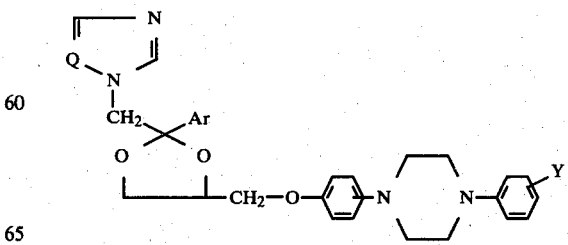

and the pharmaceutically acceptable acid addition salts and stereochemically isometric forms thereof, wherein:

Q is a member selected from the group consisting of CH and N;

Ar is a member selected from the group consisting of phenyl, thienyl, halothienyl and substituted phenyl, said substituted phenyl having from 1 to 3 substituents each independently selected from the group consisting of halo, lower alkyl, lower alkyloxy and trifluoromethyl; and the radical Y is a member selected from the group consisting of a 1H-pyrrol-1-yl radical of the formula

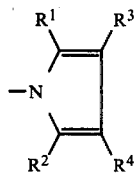

(a)

wherein $R^1$, $R^2$, $R^3$ and $R^4$ are each independently selected from the group consisting of hydrogen, lower alkyl, aryl and aryl lower alkyl;

a 1H-pyrazol-1-yl radical of the formula

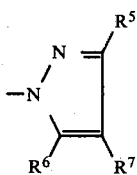

(b)

wherein $R^5$, $R^6$ and $R^7$ are each independently selected from the group consisting of hydrogen, lower alkyl, aryl and aryl lower alkyl;

a 1H-imidazol-1-yl radical of the formula

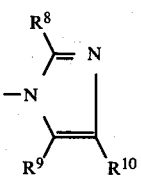

(c)

wherein $R^8$ is selected from the group consisting of hydrogen, lower alkyl, mercapto, lower alkylthio and aryl-lower alkylthio, and $R^9$ and $R^{10}$ are each independently selected from the group consisting of hydrogen, lower alkyl, aryl and aryl lower alkyl;

a 1H-1,2,4-triazol-1-yl radical of the formula

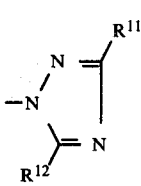

(d)

wherein either of $R^{11}$ and $R^{12}$ is selected from the group consisting of hydrogen, hydroxy, mercapto, lower alkylthio and aryl-lower alkylthio, the remaining being selected from the group consisting of hydrogen, lower alkyl and aryl-lower alkyl;

a 4H-1,2,4-triazol-4-yl radical of the formula

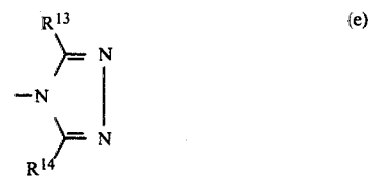

(e)

wherein $R^{13}$ is selected from the group consisting of hydrogen, mercapto, hydroxy, lower alkylthio and aryl lower alkylthio, and $R^{14}$ is selected from the group consisting of hydrogen, lower alkyl, aryl and aryl lower alkyl;

a 1H-1,2,3,4-tetrazol-1-yl radical of the formula

(g)

wherein $R^{17}$ is selected from the group consisting of hydrogen, mercapto, lower alkyl, aryl and aryl lower alkyl;

wherein said aryl as used in the foregoing definition is selected from the group consisting of phenyl and substituted phenyl, said substituted phenyl having from 1 to 3 substituents each independently selected from the group consisting of halo, lower alkyl, lower alkyloxy and trifluoromethyl.

2. A chemical compound selected from the group consisting of cis-1-{4-[2-(2,4-dichlorophenyl)-2-(1H-1,2,4-triazol-1-ylmethyl)-1,3-dioxolan-4-ylmethoxy]phenyl}-4-[4-(1H-imidazol-1-yl)phenyl]piperazine and the pharmaceutically accetable acid addition salts and stereochemically isomeric forms thereof.

3. A chemical compound selected from the group consisting of cis-1-{4-[2-(2,4-dichlorophenyl)-2-(1H-imidazol-1-ylmethyl)-1,3-dioxolan-4-ylmethoxy]phenyl}-4-[4-(1H-1,2,4-triazol-1-yl)phenyl]piperazine and the pharmaceutically acceptable acid addition salts and stereochemically isomeric forms thereof.

4. A chemical compound selected from the group consisting of cis-1-{4-[2-(2,4-dichlorophenyl)-2-(1H-1,2,4-triazol-1-ylmethyl)-1,3-dioxolan-4-ylmethoxy]phenyl}-4-[4-(1H-imidazol-1-yl)phenyl]piperazine and the pharmaceutically acceptable acid addition salts and stereochemically isomeric forms thereof.

5. A chemical compound selected from the group consisting of cis-1-{4-[2-(2,4-dichlorophenyl)-2-(1H-1,2,4-triazol-1-yl-methyl)-1,3-dioxolan-4-ylmethoxy]phenyl}-4-{4-[3-(methylthio)-1H-1,2,4-triazol-1-yl]phenyl}piperazine and the pharmaceutically acceptable acid addition salts and stereochemically isomeric forms thereof.

6. A chemical compound selected from the group consisting of cis-1-{4-[4-(2,4-dichlorophenyl)-2-(1H-1,2,4-triazol-1-ylmethyl)-1,3-dioxolan-4-ylmethoxy]phenyl}-4-[4-(1H-tetrazol-1-yl)phenyl]piperazine and the pharmaceutically acceptable acid addition salts and stereochemically isomeric forms thereof.

7. A composition for combatting the growth of a microorganism selected from the group consisting of fungus and bacterium comprising an inert carrier material and as an active ingredient an effective antifungal or antibacterial amount of a compound selected from the group consisting of an azole derivative having the formula

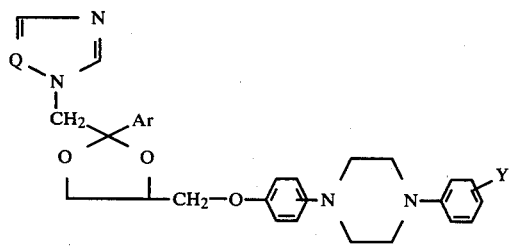

and the pharmaceutically acceptable acid addition salts and stereochemically isomeric forms thereof, wherein:

Q is a member selected from the group consisting of CH and N;

Ar is a member selected from the group consisting of phenyl, thienyl, halothienyl and substituted phenyl, said substituted phenyl having from 1 to 3 substituents each independently selected from the group consisting of halo, lower alkyl, lower alkyloxy and trifluoromethyl; and the radical Y is a member selected from the group consisting of a 1H-pyrrol-1-yl radical of the formula

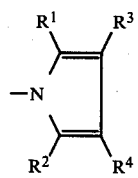

(a)

wherein $R^1$, $R^2$, $R^3$ and $R^4$ are each independently selected from the group consisting of hydrogen, lower alkyl, aryl and aryl lower alkyl;

a 1H-pyrazol-1-yl radical of the formula

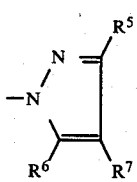

(b)

wherein $R^5$, $R^6$ and $R^7$ are each independently selected from the group consisting of hydrogen, lower alkyl, aryl and aryl lower alkyl;

a 1H-imidazol-1-yl radical of the formula

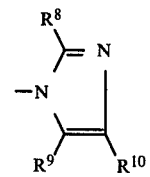

(c)

wherein $R^8$ is selected from the group consisting of hydrogen, mercapto, lower alkylthio and aryl lower alkylthio, and $R^9$ and $R^{10}$ are each independently selected from the group consisting of hydrogen, lower alkyl, aryl and aryl lower alkyl;

a 1H-1,2,4-triazol-1-yl radical of the formula

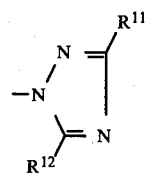

(d)

wherein either of $R^{11}$ and $R^{12}$ is selected from the group consisting of hydrogen, hydroxy, mercapto, lower alkylthio and aryl-lower alkylthio, the remaining being selected from the group consisting of hydrogen, lower alkyl and aryl-lower alkyl;

a 4H-1,2,4-triazol-4-yl radical of the formula

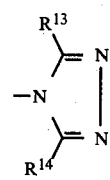

(e)

wherein $R^{13}$ is selected from the group consisting of hydrogen, mercapto, hydroxy, lower alkylthio and aryl lower alkylthio, and $R^{14}$ is selected from the group consisting of hydrogen, lower alkyl, aryl and arylllower alkyl;

a 1H-1,2,3,4-tetrazol-1-yl radical of the formula

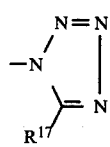

(g)

wherein $R^{17}$ is selected from the group consisting of hydrogen, mercapto, lower alkyl, aryl and aryl lower alkyl;

wherein said aryl as used in the foregoing definition is selected from the group consisting of phenyl and substituted phenyl, said substituted phenyl having from 1 to 3 substituents each independently selected from the group consisting of halo, lower alkyl, lower alkyloxy and trifluoromethyl.

* * * * *